United States Patent
Dugar et al.

(10) Patent No.: US 7,232,824 B2
(45) Date of Patent: Jun. 19, 2007

(54) QUINAZOLINE DERIVATIVES AS MEDICAMENTS

(75) Inventors: Sundeep Dugar, San Jose, CA (US); Sarvajit Chakravarty, Mountain View, CA (US); Alison Murphy, Milpitas, CA (US); Glenn McEnroe, San Mateo, CA (US); Aurelia Conte, Loerrach (DE); John J. Perumattam, Los Altos, CA (US)

(73) Assignee: Scios, Inc., Mountain View, CA (US)

( * ) Notice: Subject to any disclaimer, the term of this patent is extended or adjusted under 35 U.S.C. 154(b) by 150 days.

(21) Appl. No.: 10/957,183

(22) Filed: Sep. 30, 2004

(65) Prior Publication Data

US 2005/0096333 A1  May 5, 2005

Related U.S. Application Data

(60) Provisional application No. 60/507,910, filed on Sep. 30, 2003.

(51) Int. Cl.
C07D 239/94 (2006.01)
C07D 471/04 (2006.01)

(52) U.S. Cl. .................. 514/249; 514/252.17; 514/258; 544/258; 544/279; 544/293

(58) Field of Classification Search ................ 514/249, 514/259, 258, 252.17; 544/293, 258, 279
See application file for complete search history.

(56) References Cited

U.S. PATENT DOCUMENTS

| | | | |
|---|---|---|---|
| 4,480,883 A | 11/1984 | Young | 312/220 |
| 5,034,393 A | 7/1991 | Hackler et al. | 514/258 |
| 5,430,148 A | 7/1995 | Webber et al. | 514/238 |
| 5,475,001 A | 12/1995 | Barker | 514/183 |
| 5,616,582 A | 4/1997 | Barker | 514/234.5 |
| 5,719,157 A | 2/1998 | Sohda et al. | 514/266.31 |
| 5,721,237 A | 2/1998 | Myers et al. | 514/266.1 |
| 6,184,226 B1 | 2/2001 | Chakravarty et al. | 514/266.22 |
| 6,251,912 B1 | 6/2001 | Wissner et al. | 514/228.2 |
| 6,355,678 B1 | 3/2002 | Uckun et al. | 514/521 |
| 6,476,031 B1* | 11/2002 | Chakravarty et al. | 514/249 |

FOREIGN PATENT DOCUMENTS

| | | |
|---|---|---|
| WO | WO 96/40143 | 12/1996 |
| WO | WO 97/26252 | 7/1997 |
| WO | WO 98/06715 | 2/1998 |
| WO | WO 98/07425 | 2/1998 |
| WO | WO 00/12497 | 3/2000 |
| WO | WO-03/097615 | 11/2003 |
| WO | WO-2004/047818 | 6/2004 |

OTHER PUBLICATIONS

International Search Report for PCT/US04/32430, mailed on Apr. 4, 2005, 2 pages.
Birnbaumer, Cell (1992) 71:1069-1072.
Crawford et al., Cell (1998) 93:1159-1170.
Lawrence, Eur. Cytokine Network (1996) 7:363-374.
Lin et al., Cell (1992) 68:775-785.
Lopez-Casillas, Cell (1991) 67:785-795.
Lyons and Moses, Eur. J. Biochem. (1990) 187:467-473.
Massague, Ann. Rev. Cell Biol. (1990) 6:597-641.
Massague, Ann. Rev. Biochem. (1998) 67:753-791.
Massague, Cell (1992) 69:1067-1070.
Munger et al., Cell (1999) 96:319-328.
Munger et al., Kidney Int'l. (1997) 51:1376-1382.
Sporn and Roberts, Handbook of Experimental Pharmacology (1990) 95:419-472.
Wahl et al., Immunol. Today (1989) 10:258-261.
Wang et al., Cell (1991) 67:797-805.
Wrana et al., Cell (1992) 71:1003-1014.

* cited by examiner

*Primary Examiner*—James O. Wilson
*Assistant Examiner*—Paul V. Ward
(74) *Attorney, Agent, or Firm*—Morrison & Foerster LLP

(57) ABSTRACT

Quinazoline derivatives have the formula:

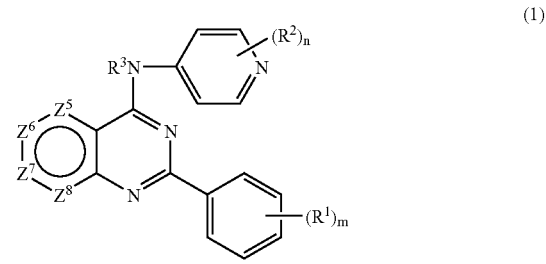

(1)

or the pharmaceutically acceptable salts thereof;
wherein each of $Z^5$, $Z^6$, $Z^7$ and $Z^8$ is N or CH and wherein one or two $Z^5$, $Z^6$, $Z^7$ and $Z^8$ are N and wherein two adjacent Z positions cannot be N;
wherein m and n are each independently 0–3;
wherein $R^1$ is independently OH, SH, $NH_2$, OR, SR, NHR, halo or R-halide;
wherein two adjacent $R^1$ groups may be joined to form an aliphatic hetero cycle ring of 5–6 members;
wherein $R^2$ is independently R, halo, R-halide, OR-halide, $NH_2$, $CONH_2$ or CONHR;
wherein R is optionally substituted $C_1$–$C_{12}$ alkyl, $C_1$–$C_{12}$ alkenyl, $C_1$–$C_{12}$ alkynyl, or aryl $C_1$–$C_{12}$ alkyl, containing 0–4 heteroatoms in place of a carbon in the carbon backbone, where the optional substituents are =O, =N, or OH; and
wherein $R^3$ is H or $CH_3$.

Such compounds are useful in pharmaceutical compositions and methods of treating conditions characterized by enhanced TGFβ activity.

15 Claims, No Drawings

US 7,232,824 B2

QUINAZOLINE DERIVATIVES AS MEDICAMENTS

RELATED APPLICATIONS

The application claims priority to U.S. Provisional Patent Application No. 60/507,910, filed Sep. 30, 2003, which is hereby incorporated by reference in its entirety.

FIELD OF THE INVENTION

The invention relates to treating various disorders associated with enhanced activity of transforming growth factor beta (TGF-β). More specifically, it concerns compounds that are related to quinazoline as useful in these methods

BACKGROUND ART

Transforming growth factor-beta receptor kinase (TGF-β) denotes a family of proteins, TGF-β1, TGF-β2, and TGF-β3, which are pleiotropic modulators of cell growth and differentiation, embryonic and bone development, extracellular matrix formation, hematopoiesis, immune and inflammatory responses (Roberts and Sporn *Handbook of Experimental Pharmacology* (1990) 95:419–58; Massague et al. *Ann Rev Cell Biol* (1990) 6:597–646). Other members of this superfamily include activin, inhibin, bone morphogenic protein, and Mullerian inhibiting substance. TGF-β initiates an intracellular signaling pathway leading ultimately to the expression of genes that regulate the cell cycle, control proliferative responses, or relate to extracellular matrix proteins that mediate outside-in cell signaling, cell adhesion, migration and intercellular communication.

Therefore, inhibitors of the TGF-β intracellular signaling pathway are useful treatments for fibroproliferative diseases. Specifically, fibroproliferative diseases include kidney disorders associated with unregulated TGF-β activity and excessive fibrosis including glomerulonephritis (GN), such as mesangial proliferative GN, immune GN, and crescentic GN. Other renal conditions include diabetic nephropathy, renal interstitial fibrosis, renal fibrosis in transplant patients receiving cyclosporin, and HIV-associated nephropathy. Collagen vascular disorders include progressive systemic sclerosis, polymyositis, scleroderma, dermatomyositis, eosinophilic fascitis, morphea, or those associated with the occurrence of Raynaud's syndrome. Lung fibroses resulting from excessive TGF-β activity include adult respiratory distress syndrome, idiopathic pulmonary fibrosis, and interstitial pulmonary fibrosis often associated with autoimmune disorders, such as systemic lupus erythematosus and scleroderma, chemical contact, or allergies. Another autoimmune disorder associated with fibroproliferative characteristics is rheumatoid arthritis.

Eye diseases associated with a fibroproliferative condition include retinal reattachment surgery accompanying proliferative vitreoretinopathy, cataract extraction with intraocular lens implantation, and post glaucoma drainage surgery.

PCT applications WO98/06715, WO98/07425, and WO 96/40143, all of which are incorporated herein by reference, describe compounds which are either imidazoles or are indoles substituted at the 3- or 4-position with a piperazine ring linked through a carboxamide linkage. Additional compounds which are conjugates of piperazines with indoles are described as insecticides in WO97/26252, also incorporated herein by reference.

The compounds of the invention are quinazoline derivatives. Other quinazoline compounds for other uses have been described. U.S. Pat. No. 5,721,237 assigned to Rhone-Poulenc Rorer is directed to methods for selective treatment of cell growth and differentiation characterized by activity of human epidermal growth factor (EGF) receptor type II using quinazoline substituted only in the 4-position with an aromatic moiety optionally coupled to the quinazoline through a linking moiety. U.S. Pat. No. 4,480,883 describes compounds that exhibit tyrosine kinase inhibition activity wherein the heterocyclic portion of a quinazoline or other fused ring nitrogen-containing aromatic system is substituted only once with an aromatic moiety, again optionally coupled through a linker. U.S. Pat. No. 5,616,582 assigned to Zeneca describes tyrosine kinase inhibitors which are quinazolines linked through an amino group at the 4-position to a substituted or unsubstituted phenyl. These compounds contain no substituents at position 2. U.S. Pat. No. 5,475,001 also assigned to Zeneca describes similar compounds with the same activity. U.S. Pat. No. 5,430,148 assigned to Agouron Pharmaceutical describes antiproliferative substituted quinazolinones and their counterparts wherein the keto group is replaced by a sulfone.

U.S. Pat. No. 5,719,157 to Takeda Chemical Industries describes pharmaceutical compositions for inhibiting bone resorption which include 4-phenyl quinoline derivatives which may further be substituted at the 2-position with an optionally substituted hydrocarbon group or an optionally substituted heterocyclic group.

U.S. Pat. No. 5,034,393 issued to Hackler et al. describes fungicides encompassing a genus of pyridopyrimidine, pteridine, pyrimidopyrimidine, pyrimidopyridazine, and pyrimidotriazine derivatives.

None of the foregoing patents describes quinazoline derivatives which specifically inhibit TGF-β.

U.S. Pat. No. 6,184,226 assigned to the assignee of the present application, Scios Inc., describes compounds and methods of inhibiting p38 kinase activity using substituted quinazolines or quinazoline derivatives having an N in the quinazoline backbone at the 8-position. These compounds include an N-containing substituent at the 1-position that links the quinazoline or derivative thereof to an optionally substituted phenyl, pyridyl, indolyl, or pyrimidinyl group. PCT application WO 00/12497, also assigned to the assignee of the present application, Scios Inc., describes compounds and methods of inhibiting p38-α and TGF-β using substituted quinazolines or quinazoline derivatives wherein up to two N's replace up to two C's at the 5-position to the 8-position in the quinazoline backbone. These compounds include a linker at the 1-position that links the quinazoline or derivative thereof to an optionally substituted cyclic aliphatic cyclic heteroaliphatic, aromatic or heteroaromatic group. These compounds also include an optionally substituted non-interfering substituent at the 2-position. There is no indication which species in this genus of compounds have a particularly high TGF-β inhibition activity, which species have a selective activity for TGF-β inhibition over p38, nor which species have suppressed epidermal growth factor (EGF) receptor tyrosine kinase activity, which EGF receptor tyrosine kinase activity has been associated with quinazolines and derivatives thereof, see e.g., U.S. Pat. No. 6,251,912. As kinases have similar domains, it would be useful to have compounds with greater selectivity for TGF-β, preferably with greater selectivity over p38 or EGF receptor.

DISCLOSURE OF THE INVENTION

The invention is directed to methods and compounds useful in treating conditions that are characterized by enhanced TGF-β activity, preferably selective activity for TGF-β inhibition over p38 kinase, and which preferably have suppressed EGFR activity. These conditions include fibro-proliferative diseases, various cancers, and certain cardiovascular disorders as further described below.

Compounds of the invention have been found to inhibit TGF-β and are thus useful in treating diseases mediated by these activities. The compounds of the invention are of the formula

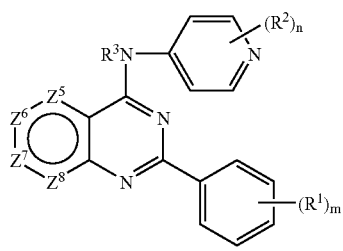

(1)

or the pharmaceutically acceptable salts thereof;

wherein each of $Z^5$, $Z^6$, $Z^7$ and $Z^8$ is N or CH and wherein one or two $Z^5$, $Z^6$, $Z^7$ and $Z^8$ are N and wherein two adjacent Z positions cannot be N;

wherein m and n are each independently 0–3;

wherein two adjacent $R^1$ groups may be joined to form an aliphatic heterocycle ring of 5–6 members;

wherein each $R^1$ is independently OH, SH, $NH_2$, OR, SR, NHR, halo or R-halide;

wherein each $R^2$ is independently R, halo, R-halide, OR-halide, $NH_2$, $CONH_2$ or CONHR;

wherein R is optionally substituted $C_1$–$C_{12}$ alkyl, $C_1$–$C_{12}$ alkenyl, $C_1$–$C_{12}$ alkynyl, or aryl $C_1$–$C_{12}$ alkyl, containing 0–4 heteroatoms in place of a carbon in the carbon backbone, where the optional substituents are =O, =N, or OH; and wherein $R^3$ is H or $CH_3$;

with the following provisos:

when $Z^5$–$Z^7$ are CH and $Z^8$ is N, when $R^3$ is H, and when the pyridyl is unsubstituted, then m is 1–3 (i.e., the phenyl is substituted) and if m is 1, then $R^1$ is not 2-fluoro or 2-Chloro;

when $Z^5$ and $Z^8$ are N and $Z^6$ and $Z^7$ are CH, when $R^3$ is H, and when the pyridyl is unsubstituted, then the phenyl is substituted; and when $Z^5$ is N and $Z^6$–$Z^8$ are CH, when $R^3$ is H, and when the pyridyl is unsubstituted, then the phenyl is substituted.

Pharmaceutical compositions and methods of the invention use compounds defined above and also those having the formula:

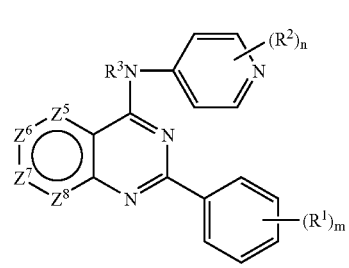

(1)

or the pharmaceutically acceptable salts thereof;

wherein each of $Z^5$, $Z^6$, $Z^7$ and $Z^8$ is N or CH and wherein one or two $Z^5$, $Z^6$, $Z^7$ and $Z^8$ are N and wherein two adjacent Z positions cannot be N;

wherein m and n are each independently 0–3;

wherein two adjacent $R^1$ groups may be joined to form an aliphatic hetero cycle ring of 5–6 members;

wherein each $R^1$ is independently OH, SH, $NH_2$, OR, SR, NHR, halo or R-halide;

wherein each $R^2$ is independently R, halo, R-halide, OR-halide, $NH_2$, $CONH_2$ or CONHR;

wherein R is optionally substituted $C_1$–$C_{12}$ alkyl, $C_1$–$C_{12}$ alkenyl, $C_1$–$C_{12}$ alkynyl, or aryl $C_1$–$C_{12}$ alkyl, containing 0–4 heteroatoms in place of a carbon in the carbon backbone, where the optional substituents are =O, =N, or OH; and wherein $R^3$ is H or $CH_3$.

The invention is directed to methods of treating proliferative conditions using these compounds. The invention is also directed to treating conditions associated with cardiac diseases using the invention compounds.

Modes of Carrying out the Invention

The compounds of formula (1) are useful in treating conditions which are characterized by enhanced activity of TGF-β. Conditions "characterized by enhanced TGF-β activity" include those wherein TGF-β synthesis is stimulated so that TGF-β is present in enhanced amount or wherein TGF-β latent protein is undesirably activated or converted to active TGF-β protein or wherein TGF-β receptors are upregulated or wherein the TGF-β protein shows enhanced binding to cells or extracellular matrix in the location of the disease. Thus, "enhanced activity" refers to any condition wherein the effectiveness of this protein is undesirably high, regardless of the cause.

The compounds of the invention are useful in conditions where TGF-β shows enhanced activity since these compounds inhibit the activities of this protein. These conditions are those in which fibrosis and organ sclerosis are caused by, or accompanied by, inflammation, oxidation injury, hypoxia, altered temperature or extracellular osmolarity, conditions causing cellular stress, apoptosis or necrosis. These conditions include ischemia-reperfusion injury, congestive heart failure, progressive pulmonary and bronchial fibrosis, hepatitis, arthritis, inflammatory bowel disease, glomerular sclerosis, interstitial renal fibrosis, chronic scarring diseases of the eyes, bladder and reproductive tract, bone marrow dysplasia, chronic infectious or autoimmune states and traumatic or surgical wounds. These conditions, of course, would be benefited by compounds which inhibit TGF-β. Methods of treatment with the compounds of the invention are further discussed below.

In addition, the compounds of the invention are useful in treating conditions which are characterized by enhanced activity of TGF-β which conditions are preferably not characterized by over activity of p38 or EGF, and thus have greater selectivity over p38 or EGF receptor.

THE INVENTION COMPOUNDS

The compounds useful in the invention are derivatives of quinazoline and related compounds containing mandatory substituents at positions corresponding to the 2- and 4-positions of the quinazoline. Preferably, the compounds of the invention include a pteridine or pyridopyrimidine nucleus. Pteridine and 8-pyrido pyrimidine nuclei are preferred. Thus, in one embodiment $Z^5$ and $Z^8$ are N, and $Z^6$ and $Z^7$ are CH. However in all cases, at least one of each of $Z^5$–$Z^8$ must be N.

The position that corresponds to the 2-position of the quinazoline contains a mandatory phenyl substituent, having 0–4 substituents, namely $(R^1)_m$, where m is 0–4.

The position that corresponds to the 4-position of the quinazoline contains a mandatory —$NR^{3-4'}$-pyridyl substituent that may optionally contain 0–4 substituents, namely $(R^2)_n$, wherein n is 0–4. Preferably, the pyridyl group is unsubstituted, i.e., n is 0. When substituted, the pyridyl moiety is preferably substituted with one or two $R^2$ substituents, preferably one $R^2$ substituent, which is an alkyl group such as methyl or ethyl; a halo group preferably bromo or iodo; or $CONH_2$ or CONHR where R is optionally substituted $C_1$–$C_{12}$ alkyl, $C_1$–$C_{12}$ alkenyl, $C_1$–$C_{12}$ alkynyl, or aryl $C_1$–$C_{12}$ alkyl, containing 0–4 heteroatoms in place of a carbon in the carbon backbone, where the optional substituents are =O, =N, or OH; $R^2$ is preferably a 3' substituent of the pyridyl moiety. In a particularly preferred embodiment, m is 0, n is 1, and $R^2$ is positioned at the 3' position of the pyridyl moiety.

In another embodiment, n is 1, and $R^2$ is methyl, F, or $CONH_2$, preferably, at the 1' or 2' position.

The $R^1$ substituent(s) on the phenyl moiety preferably include minimally bulky groups. In one aspect, R is halo, lower alkyl, lower alkoxy, and lower alkyl halide groups. Preferably such groups include one or more halo, such as Cl, F, Br, and I which may be the same or different if more than two halo groups are present. In another aspect, $R^1$ is an alkyl halide containing 1–3 halides, preferably methyl halide and even more preferably trifluoro methyl. In another aspect, $R^1$ is an O-alkylaryl group such as O-benzyl. In another aspect, $R^1$ is R, OH, SH, $NH_2$, OR, SR or NHR, where R is optionally substituted $C_1$–$C_{12}$ alkyl, $C_1$–$C_{12}$ alkenyl, $C_1$–$C_{12}$ alkynyl, or aryl $C_1$–$C_{12}$ alkyl, containing 0–4 heteroatoms in place of a carbon in the carbon backbone, where the optional substituents are =O, =N, or OH. Preferably, R is a lower alkyl, preferably Cl-6, more preferably Cl-3 alkyl, and even more preferably, methyl, ethyl, propyl or isopropyl. Two adjacent R groups may join to make an aliphatic or hetero aliphatic ring fused to the 2-phenyl. Preferably, if a fused ring is present it has 5 or 6 members, preferably 5 members and contains 1 or more heteroatoms such as N, S or O, and preferably 1 or 2 O. Preferably, the fused ring is 1, 3 dioxolane fused to phenyl at the 4 and 5 position of the phenyl ring. Preferred R groups are F, Cl, Br, I, $CH_3$, $OCH_3$, $CF_3$, $OCH(CH_3)_2$, $OCH_2CH_3$, or O-benzyl. Preferably, is 0, 1 or 2.

The $R^1$ group or groups that are bound to the 2-phenyl group may be bound at any available position of the phenyl ring. Preferably the $R^1$ group is bound at the position meta relative to the phenyl's attachment point on the quinazoline derivative nucleus. Also, in a preferred embodiment when phenyl is substituted with two groups, the groups are bound at the ortho and meta positions relative to the phenyl's attachment to the quinazoline derivative, more preferably at non-adjacent ortho and meta positions. Other embodiments include such groups at the ortho or para positions. A phenyl substituted at both meta positions or adjacent ortho and meta positions are contemplated if two groups are present. Alternatively, two groups may form a fused ring preferably attached at the meta and para positions relative to the phenyl's attachment to the quinazoline derivative. Also it is contemplated the phenyl is unsubstituted.

For compounds containing pyridopyrimidine as the nucleus, when the 6- or 7-isomers thereof are present, i.e. the nitrogen is in position 6 or 7 of pyridopyrimidine, the phenyl preferably is unsubstituted, or preferably contains one halo substituent, preferably chlorine, and preferably attached at the meta position relative to the phenyl's attachment to the pyridopyrimidine moiety.

Preferably, the phenyl is substituted, preferably with halo, more preferably one or two halos, and even more preferably chloro at the meta or para positions relative to the phenyl's attachment to the pyridopyrimidine moiety or dichloro at both meta positions; or more preferably substituted with fluoro, preferably difluoro, preferably at the ortho and meta positions relative to the phenyl's attachment to the pyridopyrimidine moiety; or more preferably bromo, preferably at the meta position relative to the phenyl's attachment to the pyridopyrimidine moiety; or more preferably iodo, preferably at the meta position relative to the phenyl's attachment to the pyridopyrimidine moiety.

In another preferred embodiment of compounds containing 8-pyridopyrimidine, the phenyl group is substituted with two or more different halo substituents, preferably disubstituted, and preferably contains fluoro and chloro, and more preferably disubstituted at the non-adjacent ortho and meta positions relative to the phenyl's attachment to the pyridopyrimidine moiety, more preferably where fluoro is at the ortho position and chloro is at the meta position relative to the phenyl's attachment to the pyridopyrimidine moiety; or preferably is disubstituted with fluoro and bromo, preferably at the non-adjacent ortho and meta positions relative to the phenyl's attachment to the pyridopyrimidine moiety, more preferably where fluoro is at the ortho position and bromo is at the meta position relative to the phenyl's attachment to the pyridopyrimidine moiety In another preferred embodiment in compounds containing 8-pyridopyrimidine, the phenyl group is substituted, preferably at one or two positions, and is preferably substituted with alkoxy or arylaryloxy, preferably methoxy, ethoxy isopropoxy, or benzoxy, and preferably at the ortho or meta position relative to the phenyl's attachment to the pyridopyrimidine moiety. In another embodiment in compounds containing 8-pyridopyrimidine, the phenyl is preferably substituted with alkyl, preferably methyl, and preferably at the meta position relative to the phenyl's attachment to the pyridopyrimidine moiety.

In another preferred embodiment in compounds containing 8-pyridopyrimidine, two or more $R^1$ substituents may join to form a fused ring. Preferably the fused ring is a dioxolane ring, more preferably a 1,3-dioxolane ring, fused to the phenyl ring at the meta and para positions relative to the phenyl's attachment to the pyridopyrimidine moiety.

In another preferred embodiment of compounds containing 8-pyridopyrimidine, the phenyl group is substituted with two or more different substituents, preferably disubstituted, and preferably chloro and methoxy, and preferably disubstituted at the non-adjacent ortho and meta positions relative to the phenyl's attachment to the pyridopyrimidine moiety, more preferably where methoxy is at the ortho position and chloro is at the meta position relative to the phenyl's attachment to the pyridopyrimidine moiety; or preferably is disubstituted with fluoro and methoxy, preferably at the adjacent ortho and meta positions relative to the phenyl's attachment to the pyridopyrimidine moiety, more preferably where fluoro is at the ortho position and methoxy is at the meta position relative to the phenyl's attachment to the pyridopyrimidine moiety.

In addition, in compounds containing the pteridine nucleus, the phenyl group preferably contains at least one halo substituent at the ortho, meta or para positions relative to the phenyl's attachment to the pteridine moiety. In a more preferred embodiment, the phenyl group contains one chloro group at the ortho or meta positions relative to the phenyl's attachment to the pteridine moiety; one fluoro group at the ortho, meta or para positions relative to the phenyl's attachment to the pteridine moiety; or one bromo or iodo at the meta position relative to the phenyl's attachment to the pteridine moiety. In another preferred embodiment, the phenyl group contains two halo groups preferably difluoro, preferably disubstituted at the non-adjacent ortho and meta positions relative to the phenyl's attachment to the pteridine moiety. In one aspect, the two halo groups are preferably dichloro, preferably disubstituted at the adjacent ortho and meta positions relative to the phenyl's attachment to the pteridine moiety. In another aspect, the two halo groups are preferably fluoro and chloro, preferably disubstituted at the adjacent or non-adjacent ortho and meta positions relative to the phenyl's attachment to the pteridine moiety, preferably where the fluoro is at the ortho position, and the chloro is at either meta position, and even more preferably where the chloro is at the non-adjacent meta position. In yet another aspect, the two halo groups are preferably fluoro and bromo preferably substituted at the non-adjacent ortho and meta positions relative to the phenyl's attachment to the pteridine moiety, preferably where the fluoro is at the ortho position, and the bromo is at the non-adjacent meta position.

In another preferred embodiment in compounds containing pteridine, the phenyl group is substituted, preferably at one or more positions, preferably one position, and more preferably with alkoxy, even more preferably with methoxy, and preferably at the ortho or meta position relative to the phenyl's attachment to the pteridine moiety. In another embodiment in compounds containing pteridine, the phenyl is preferably substituted with haloalkyl, preferably trifluoromethyl, and preferably at the meta position relative to the phenyl's attachment to the pteridine moiety.

In another preferred embodiment of compounds containing pteridine, the phenyl group is substituted with two or more different substituents, preferably two substituents, and preferably disubstituted with halo and haloalkyl, more preferably fluoro and trifluoromethyl, and preferably disubstituted at the non-adjacent ortho and meta positions relative to the phenyl's attachment to the pteridine moiety, more preferably where fluoro is at the ortho position and trifluoromethyl is at the meta position relative to the phenyl's attachment to the pteridine moiety.

The pyridyl moiety may be substituted with O–3 $R^2$ groups. Preferably, $R^2$ is independently halo, alkyl, alkenyl, alkynyl, acyl or hetero-forms thereof. More preferably $R^2$ is lower alkyl (1–3C), halo such as Br, I, Cl or F. Even more preferably, $R^2$ is methyl, ethyl, bromo, iodo, $CONH_2$, or CONHR wherein R is optionally substituted $C_1$–$C_{12}$ alkyl, $C_1$–$C_{12}$ alkenyl, $C_1$–$C_{12}$ alkynyl, or aryl $C_1$–$C_{12}$ alkyl, containing 0–4 heteroatoms in place of a carbon in the carbon backbone, where the optional substituents are =O, =N, or OH. Most preferably, n is O; that is, the pyridyl moiety is unsubstituted.

The following provisos apply to the inventive compounds:

when $Z^5$–$Z^7$ are CH and $Z^8$ is N, when $R^3$ is H, and when the pyridyl is unsubstituted, then m is 1–3 (i.e., the phenyl is substituted) and if m is 1, then $R^1$ is not 2-fluoro or 2-Chloro;

when $Z^5$ and $Z^8$ are N and $Z^6$ and $Z^7$ are CH, when $R^3$ is H, and when the pyridyl is unsubstituted, then the phenyl is substituted; and when $Z^5$ is N and $Z^6$–$Z^8$ are CH, when $R^3$ is H, and when the pyridyl is unsubstituted, then the phenyl is substituted.

As used herein, "hydrocarbyl residue" refers to a residue which contains only carbon and hydrogen. The residue may be aliphatic or aromatic, straight-chain, cyclic, branched, saturated or unsaturated. The hydrocarbyl residue, when indicated, may contain heteroatoms over and above the carbon and hydrogen members of the substituent residue. Thus, when specifically noted as containing such heteroatoms, the hydrocarbyl residue may also contain carbonyl groups, amino groups, hydroxyl groups and the like, or contain heteroatoms within the "backbone" of the hydrocarbyl residue.

As used herein, the term "alkyl," "alkenyl" and "alkynyl" include straight- and branched-chain and cyclic monovalent substituents. Examples include methyl, ethyl, isobutyl, isopropyl, cyclohexyl, cyclopentylethyl, 2-propenyl, 3-butynyl, and the like. Typically, the alkyl, alkenyl and alkynyl substituents contain 1–12C (alkyl) or 2–12C (alkenyl or alkynyl). Preferably they contain lower alkyl such as 1–6C (alkyl) or 1–3C (alkyl) or 2–6C (alkenyl or alkynyl). Heteroalkyl, heteroalkenyl and heteroalkynyl are similarly defined but may contain 1–2 O, S or N heteroatoms or combinations thereof within the backbone residue.

As used herein, "acyl" encompasses the definitions of alkyl, alkenyl, alkynyl and the related hetero-forms which are coupled to an additional residue through a carbonyl group.

"Aromatic" moiety refers to a monocyclic or fused bicyclic moiety such as phenyl or naphthyl; "heteroaromatic" also refers to monocyclic or fused bicyclic ring systems containing one ore more heteroatoms selected from O, S and N. The inclusion of a heteroatom permits inclusion of 5-membered rings as well as 6-membered rings. Thus, typical aromatic systems include pyridyl, pyrimidinyl, indolyl, benzimidazolyl, benzotriazolyl, isoquinolyl, quinolyl, benzothiazolyl, benzofuranyl, thienyl, furyl, pyrrolyl, thiazolyl, oxazolyl, imidazolyl and the like. Any monocyclic or fused ring bicyclic system which has the characteristics of aromaticity in terms of electron distribution throughout the ring system is included in this definition. Typically, the ring systems contain 5–12 ring member atoms.

Similarly, "arylalkyl" and "heteroalkyl" refer to aromatic and heteroaromatic systems which are coupled to another residue through a carbon chain, including substituted or unsubstituted, saturated or unsaturated, carbon chains, typically of 1–12C or preferably 1–6C. These carbon chains may also include a carbonyl group, thus making them able to provide substituents as an acyl moiety.

As used herein "halo," "halide" or "halogens", include the chloro, fluoro, bromo and iodo, and may refer to one or more halides on a particular moiety. For example, R-halide, where R is alkyl, may refer to $CFH_2$, $CF_2H$ or $CF_3$.

The pyridyl moiety, may also comprise two substituents which, when together, form a 5–7 membered carbocyclic or heterocyclic aliphatic ring. In a preferred embodiment, the compound has the formula:

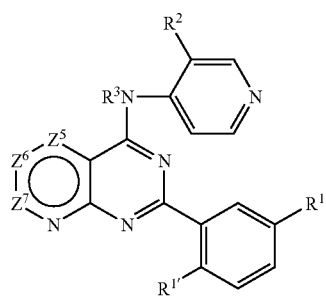

or the pharmaceutically acceptable salts thereof;

wherein each of $Z^5$, $Z^6$ and $Z^7$ is N or CH and wherein one or two $Z^5$, $Z^6$ and $Z^7$ are N and wherein two adjacent Z positions cannot be N;

wherein $R^1$ is F, Cl, Br, I or $CH_3$;

wherein $R^{1'}$ is Br, F or Cl; and wherein $R^2$ is not present, is $CH_3$ or is an electron-withdrawing group.

An electron-withdrawing group is a term known in the art, and encompasses a group that is more electronegative than carbon, and thus has an electron-withdrawing inductive effect. Examples of such groups are F, Cl, $OCF_2H$, $OCF_3$, $CF_3$, CONHR or $CONH_2$.

The compounds of formula (1) may be supplied in the form of their pharmaceutically acceptable acid-addition salts including salts of inorganic acids such as hydrochloric, sulfuric, hydrobromic, or phosphoric acid or salts of organic acids such as acetic, tartaric, succinic, benzoic, salicylic, and the like. If a carboxyl moiety is present on the compound of formula (1), the compound may also be supplied as a salt with a pharmaceutically acceptable cation, or may be supplied as an ester or free base.

Administration and Use

The compounds of the invention are useful among other indications in treating proliferative conditions. Thus, the compounds of formula (1) or their pharmaceutically acceptable salts are used in the manufacture of a medicament for prophylactic or therapeutic treatment of mammals, including humans, in respect of conditions characterized by excessive production of TGF-β or enhanced sensitivity to TGF-β.

The TGF-β inhibition activity is useful in treating fibroproliferative diseases, treating collagen vascular disorders, treating eye diseases associated with a fibroproliferative condition, venting excessive scarring, treating neurological conditions and other conditions that are targets for TGF-β inhibitors and in preventing excessive scarring that elicits and accompanies restenosis following coronary angioplasty, cardiac fibrosis occurring after infarction and progressive heart failure, and in hypertensive vasculopathy, and keloid formation or hypertrophic scars occurring during the healing of wounds including surgical wounds and traumatic lacerations.

Neurological conditions characterized by TGF-β production include CNS injury after traumatic and hypoxic insults, Alzheimer's disease, and Parkinson's disease.

Other conditions that are potential clinical targets for TGF-β inhibitors include myelofibrosis, tissue thickening resulting from radiation treatment, nasal polyposis, polyp surgery, liver cirrhosis, and osteoporosis.

Diseases benefited by TGF-β inhibition include cardiovascular diseases such as congestive heart failure, dilated cardiomyopathy, myocarditis, or vascular stenosis associated with atherosclerosis, angioplasty treatment, or surgical incisions or mechanical trauma; kidney diseases associated with fibrosis and/or sclerosis, including glomerulonephritis of all etiologies, diabetic nephropathy, and all causes of renal interstitial fibrosis, including hypertension, complications of drug exposure, such as cyclosporin, HIV-associated nephropathy, transplant nephropathy, chronic ureteral obstruction; hepatic diseases associated with excessive scarring and progressive sclerosis, including cirrhosis due to all etiologies, disorders of the biliary tree, and hepatic dysfunction attributable to infections such as hepatitis virus or parasites; syndromes associated with pulmonary fibrosis with consequential loss of gas exchange or ability to efficiently move air into and out of the lungs, including adult respiratory distress syndrome, idiopathic pulmonary fibrosis, or pulmonary fibrosis due to infectious or toxic agents such as smoke, chemicals, allergens, or autoimmune disease; all collagen vascular disorders of a chronic or persistent nature including progressive systemic sclerosis, polymyositis, scleroderma, dermatomyositis, fascists, or Raynaud's syndrome, or arthritic conditions such as rheumatoid arthritis; eye diseases associated with fibroproliferative states, including proliferative vitreoretinopathy of any etiology or fibrosis associated with ocular surgery such as retinal reattachment, cataract extraction, or drainage procedures of any kind; excessive or hypertrophic scar formation in the dermis occurring during wound healing resulting from trauma or surgical wounds; disorders of the gastrointestinal tract associated with chronic inflammation, such as Crohn's disease or ulcerative colitis or adhesion formation as a result of trauma or surgical wounds, polyposis or states post polyp surgery; chronic scarring of the peritoneum associated with endometriosis, ovarian disease, peritoneal dialysis, or surgical wounds; neurological conditions characterized by TGF-β production or enhanced sensitivity to TGF-β, including states post-traumatic or hypoxic injury, Alzheimer's disease, and Parkinson's disease; and diseases of the joints involving scarring sufficient to impede mobility or produce pain, including states post-mechanical or surgical trauma, osteoarthritis and rheumatoid arthritis. In addition, various cancers can be treated through therapy which inhibits TGFb.

The modulation of the immune and inflammation systems by TGF-β (Wahl et al. *Immunol Today* (1989) 10:258–61) includes stimulation of leukocyte recruitment, cytokine production, and lymphocyte effector function, and inhibition of T-cell subset proliferation, B-cell proliferation, antibody formation, and monocytic respiratory burst. TGF-β is a stimulator for the excess production of extracellular matrix proteins, including fibronectin and collagen. It also inhibits the production of enzymes that degrade these matrix proteins. The net effect is the accumulation of fibrous tissue which is the hallmark of fibroproliferative diseases.

TGF-β is active as a homodimer, but is synthesized and secreted from cells as an inactive latent complex of the mature homodimer and proregions, called latency associated protein (LAP). These proteins bind to each other through noncovalent interactions (Lyons and Moses *Eur J Biochem*

(1990) 187:467). LAP is often disulfide-linked to separate gene products, called latent TGF-β binding proteins or LTBPs. These latent forms provide stability for the mature cytokine and a means for targeting it to the extracellular matrix and cell surfaces (Lawrence *Eur Cytokine Network* (1996) 7:363–74). Activation of the latent complex occurs after secretion from cells and is believed to result from the action of proteases, such as plasmin (Munger et al. *Kidney Intl* (1997) 51:1376–82), on LAP, thrombospondin-1 binding (Crawford et al. *Cell* (1998) 93:1159–70), and binding to the integrin v6 (Munger et al. *Cell* (1999) 319–28).

Other than v6 there is a variety of cell surface proteins/ receptors that transduce the signals initiated by binding of the active TGF-β ligand to its receptors. These include types I, II, III, IV, and V. Type IV is present only in the pituitary gland while the others are ubiquitous. The binding affinities among the three isoforms for the type I and II receptors differ such that these two receptors bind TGF-β1 and TGF-β3 more tightly than TGF-β2 (Massague *Cell* (1992) 69:1067–70).

The type IV receptor or endoglin has a similar isoform binding profile in contrast to the type III receptor, betaglycan, which binds equally well to all three isoforms (Wang et al. *Cell* (1991) 67:797–805; Lopez-Casillas *Cell* (1991) 67:785–95). The type V receptor binds to IGFBP-3 and is thought to have an active kinase domain similar to the type I and II receptors. Cloning of the type I and type II receptors demonstrated the existence of cytoplasmic serine/threonine kinase domains (Wrana et al. *Cell* (1992) 71:1003–14; Lin et al. *Cell* (1992) 68:775–85; *Ibid.* 71:1069; Massague *Cell* (1992) 69:1067–70). Initiation of the TGF-β signaling pathway results from the binding of the TGF-β ligand to the extracellular domain of the type II receptor (Massague *Ann Rev Biochem* (1998) 67:753–91). The bound receptor then recruits type I receptor into a multimeric membrane complex, whereupon the constitutively active type II receptor kinase phosphorylates and activates type I receptor kinase. The function of the type I receptor kinase is to phosphorylate a receptor-associated co-transcription factor, smad-2/3, thereby releasing it into the cytoplasm where it binds to smad-4. This smad complex translocates into the nucleus, associates with a DNA-binding cofactor, such as Fast-1, binds to enhancer regions of specific genes, and activates transcription. The expression of these genes leads to the synthesis of cell cycle regulators that control proliferative responses or extracellular matrix proteins that mediate outside-in cell signaling, cell adhesion, migration, and intercellular communication.

The manner of administration and formulation of the compounds useful in the invention and their related compounds will depend on the nature of the condition, the severity of the condition, the particular subject to be treated, and the judgement of the practitioner; formulation will depend on mode of administration. As the compounds of the invention are small molecules, they are conveniently administered by oral administration by compounding them with suitable pharmaceutical excipients so as to provide tablets, capsules, syrups, and the like. Suitable formulations for oral administration may also include minor components such as buffers, flavoring agents and the like. Typically, the amount of active ingredient in the formulations will be in the range of 5%–95% of the total formulation, but wide variation is permitted depending on the carrier. Suitable carriers include sucrose, pectin, magnesium stearate, lactose, peanut oil, olive oil, water, and the like.

The compounds useful in the invention may also be administered through suppositories or other transmucosal vehicles. Typically, such formulations will include excipients that facilitate the passage of the compound through the mucosa such as pharmaceutically acceptable detergents.

The compounds may also be administered topically, for topical conditions such as psoriasis, or in formulation intended to penetrate the skin. These include lotions, creams, ointments and the like which can be formulated by known methods.

The compounds may also be administered by injection, including intravenous, intramuscular, subcutaneous or intraperitoneal injection. Typical formulations for such use are liquid formulations in isotonic vehicles such as Hank's solution or Ringer's solution.

Alternative formulations include nasal sprays, liposomal formulations, slow-release formulations, and the like, as are known in the art.

Any suitable formulation may be used. A compendium of art-known formulations is found in *Remington's Pharmaceutical Sciences*, latest edition, Mack Publishing Company, Easton, Pa. Reference to this manual is routine in the art.

The dosages of the compounds of the invention will depend on a number of factors which will vary from patient to patient. However, it is believed that generally, the daily oral dosage will utilize 0.001–100 mg/kg total body weight, preferably from 0.01–50 mg/kg and more preferably about 0.01 mg/kg–10 mg/kg. The dose regimen will vary, however, depending on the conditions being treated and the judgment of the practitioner.

It should be noted that the compounds of formula (1) can be administered as individual active ingredients, or as mixtures of several embodiments of this formula. In addition, the inhibitors of TGF-β, can be used as single therapeutic agents or in combination with other therapeutic agents. Drugs that could be usefully combined with these compounds include natural or synthetic corticosteroids, particularly prednisone and its derivatives, monoclonal antibodies targeting cells of the immune system, antibodies or soluble receptors or receptor fusion proteins targeting immune or non-immune cytokines, and small molecule inhibitors of cell division, protein synthesis, or mRNA transcription or translation, or inhibitors of immune cell differentiation or activation.

As implicated above, although the compounds of the invention may be used in humans, they are also available for veterinary use in treating animal subjects.

Synthesis of the Invention Compounds

The compounds of the invention having a pteridine nucleus may be synthesized from methyl 3-amino-2-pyrazine carboxylate as described in Reaction Scheme I. Alternatively, compounds of the invention having a pyridopyrimidine nucleus having a nitrogen at the 7 position may be synthesized from ethyl 1-benzyl-3-oxo-piperidine carboxylate-hydrochloride and benzamidine hydrochloride or analog thereof as illustrated in Reaction Scheme II. Compounds of the invention having a pyridopyrimidine nucleus where there is an N in the 6 position of the nucleus may be prepared from methyl 1-benzyl-oxo-3-piperidine carboxylate hydrochloride and benzamidine hydrochloride as shown in Reaction Scheme III. Compounds of the invention having a pyridopyrimidine nucleus having an N at the 8 position may be synthesized from 2-amino nicotinic acid methyl ester. An alternate procedure for the final step in Reaction Scheme IV is illustrated in Reaction Scheme V.

Compounds of the invention include those in Table 1.

TABLE 1

| COMPOUND # | STRUCTURE |
| --- | --- |
| 1 | (pteridine with NH-4-pyridyl at 4-position and 2-fluorophenyl at 2-position) |
| 2 | (pteridine with NH-4-pyridyl at 4-position and 3-chlorophenyl at 2-position) |
| 3 | (pteridine with NH-4-pyridyl at 4-position and 3-methoxyphenyl at 2-position) |
| 4 | (pteridine with NH-4-pyridyl at 4-position and 2-methoxyphenyl at 2-position) |
| 5 | (pteridine with NH-4-pyridyl at 4-position and 2,3-dichlorophenyl at 2-position) |

TABLE 1-continued

| COMPOUND # | STRUCTURE |
| --- | --- |
| 6 | (pteridine with NH-4-pyrimidinyl at 4-position and 3-chlorophenyl at 2-position) |
| 7 | (pteridine with N(CH$_3$)-4-pyridyl at 4-position and 3-chlorophenyl at 2-position) |
| 8 | (pteridine with NH-(3-amino-4-pyridyl) at 4-position and 3-chlorophenyl at 2-position) |
| 9 | (pteridine with NH-4-pyridyl at 4-position and 2,5-difluorophenyl at 2-position) |
| 10 | (pteridine with NH-4-pyridyl at 4-position and 2-chlorophenyl at 2-position) |

TABLE 1-continued

| COMPOUND # | STRUCTURE |
|---|---|
| 11 | (pteridine with HN-pyridin-4-yl at 4-position and 2-fluoro-3-chlorophenyl at 2-position) |
| 12 | (pteridine with HN-pyridin-4-yl at 4-position and 3-(trifluoromethyl)phenyl at 2-position) |
| 13 | (pteridine with HN-pyridin-4-yl at 4-position and 3-fluorophenyl at 2-position) |
| 14 | (pteridine with HN-pyridin-4-yl at 4-position and 2-fluoro-5-chlorophenyl at 2-position) |
| 15 | (pteridine with HN-pyridin-4-yl at 4-position and 3-bromophenyl at 2-position) |
| 16 | (pteridine with HN-pyridin-4-yl at 4-position and 2-fluoro-5-bromophenyl at 2-position) |
| 17 | (pteridine with HN-pyridin-4-yl at 4-position and 4-fluorophenyl at 2-position) |
| 18 | (pteridine with HN-pyridin-4-yl at 4-position and 2-fluoro-5-(trifluoromethyl)phenyl at 2-position) |
| 19 | (pteridine with HN-pyridin-4-yl at 4-position and 3-iodophenyl at 2-position) |

TABLE 1-continued

| COMPOUND # | STRUCTURE |
|---|---|
| 20 | (structure) |
| 21 | (structure) |
| 22 | (structure) |
| 23 | (structure) |
| 24 | (structure) |
| 25 | (structure) |
| 26 | (structure) |
| 27 | (structure) |
| 28 | (structure) |

TABLE 1-continued

| COMPOUND # | STRUCTURE |
|---|---|
| 29 | pyrido[2,3-d]pyrimidine with 4-(pyridin-4-ylamino) and 2-(benzo[1,3]dioxol-5-yl) substituents |
| 30 | pyrido[2,3-d]pyrimidine with 4-(pyridin-4-ylamino) and 2-(3-isopropoxyphenyl) substituents |
| 31 | pyrido[2,3-d]pyrimidine with 4-(pyridin-4-ylamino) and 2-(3-ethoxyphenyl) substituents |
| 32 | pyrido[2,3-d]pyrimidine with 4-(pyridin-4-ylamino) and 2-(3-benzyloxyphenyl) substituents |
| 33 | pyrido[2,3-d]pyrimidine with 4-(pyridin-4-ylamino) and 2-(3-chlorophenyl) substituents |
| 34 | pyrido[2,3-d]pyrimidine with 4-(pyridin-4-ylamino) and 2-(5-chloro-2-methoxyphenyl) substituents |
| 35 | pyrido[2,3-d]pyrimidine with 4-(pyridin-4-ylamino) and 2-(3,5-dichlorophenyl) substituents |
| 36 | pyrido[2,3-d]pyrimidine with 4-(pyridin-4-ylamino) and 2-(4-chlorophenyl) substituents |
| 37 | pyrido[2,3-d]pyrimidine with 4-(pyridin-4-ylamino) and 2-(5-chloro-2-fluorophenyl) substituents |

TABLE 1-continued

| COMPOUND # | STRUCTURE |
|---|---|
| 38 | 4-pyridylamino-pyrido[2,3-d]pyrimidine with 2-(2-fluoro-3-methoxyphenyl) substituent |
| 39 | 4-pyridylamino-pyrido[2,3-d]pyrimidine with 2-(3-bromophenyl) substituent |
| 40 | 4-pyridylamino-pyrido[2,3-d]pyrimidine with 2-(3-iodophenyl) substituent |
| 41 | 4-pyridylamino-pyrido[2,3-d]pyrimidine with 2-(5-bromo-2-fluorophenyl) substituent |
| 42 | 4-pyridylamino-pyrido[2,3-d]pyrimidine with 2-(2,5-difluorophenyl) substituent |
| 43 | 4-(3-methylpyridin-4-ylamino)-pyrido[2,3-d]pyrimidine with 2-(5-chloro-2-fluorophenyl) substituent |
| 44 | 4-(3-methylpyridin-4-ylamino)-pyrido[2,3-d]pyrimidine with 2-(3-chlorophenyl) substituent |
| 45 | 4-(3-fluoropyridin-4-ylamino)-pyrido[2,3-d]pyrimidine with 2-(5-chloro-2-fluorophenyl) substituent |

TABLE 1-continued
| COMPOUND # | STRUCTURE |
|---|---|
| 46 | 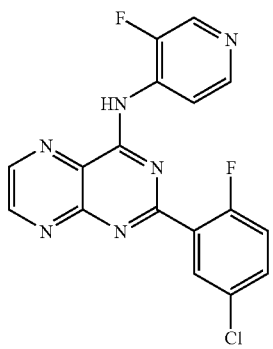 |
| 47 | |
TABLE 1-continued
| COMPOUND # | STRUCTURE |
|---|---|
| 47 | 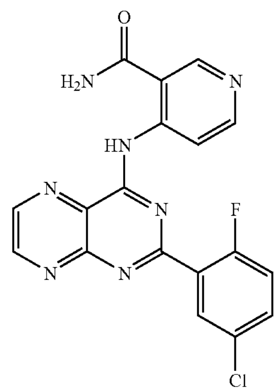 |
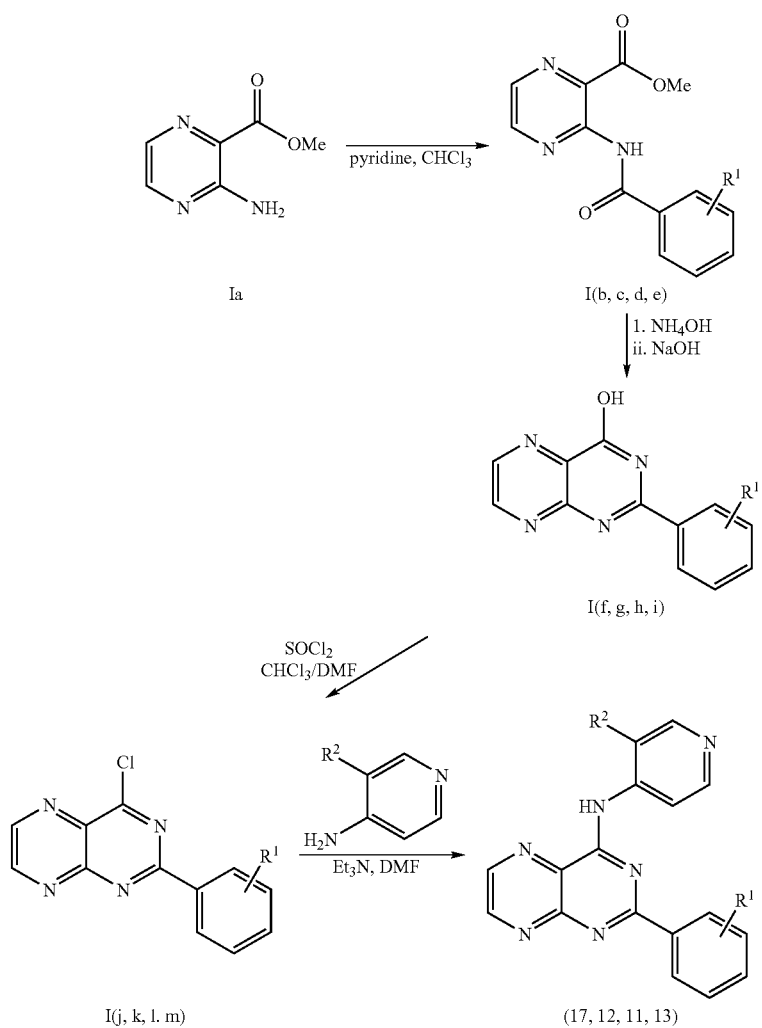
Reaction Scheme I This general scheme was used for the synthesis of compounds 1–22.
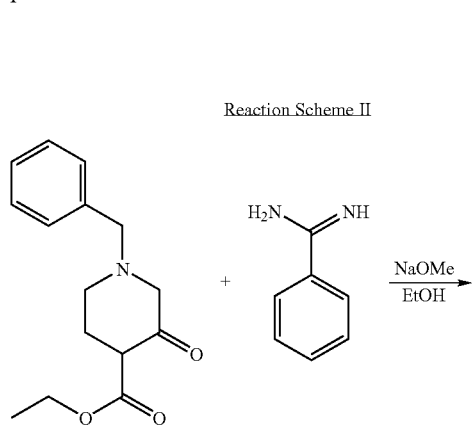
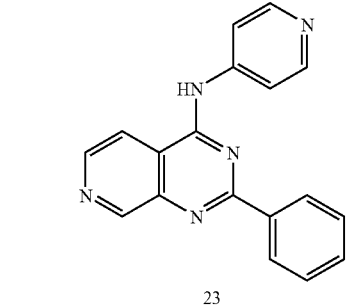
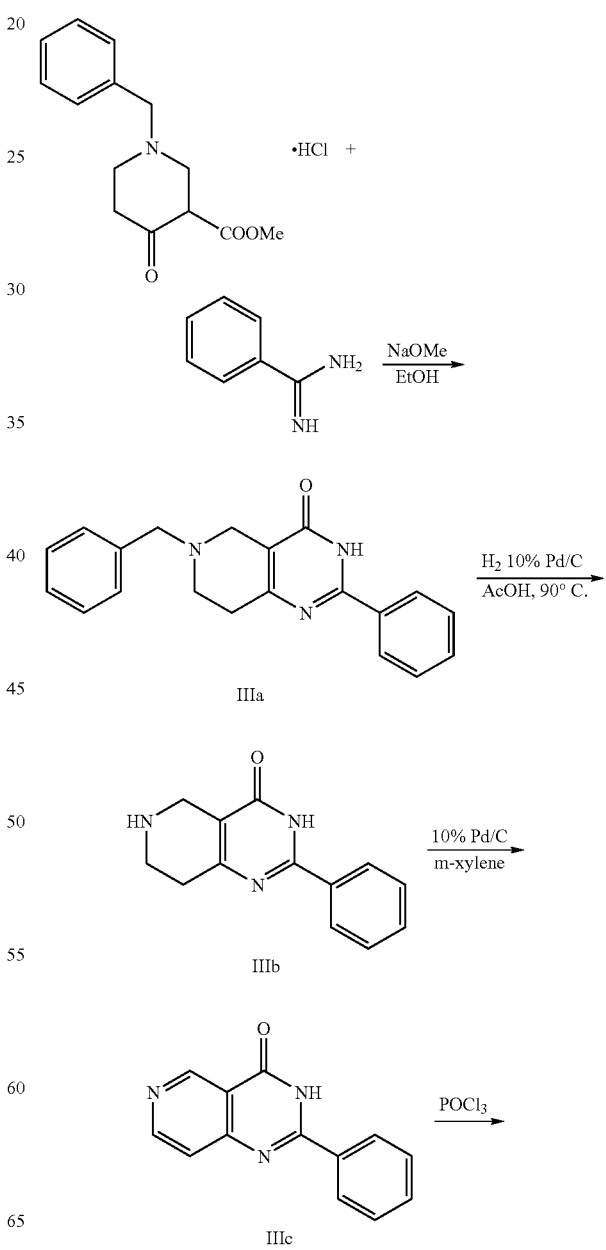

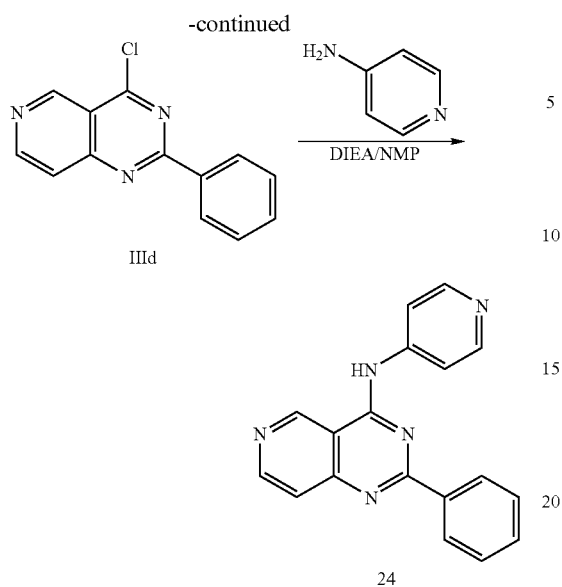
24
Reaction Scheme IV
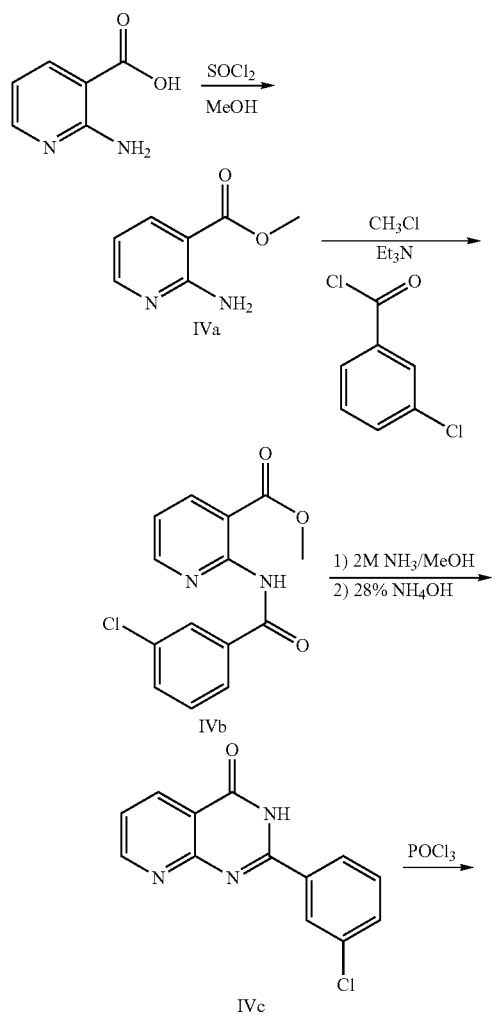
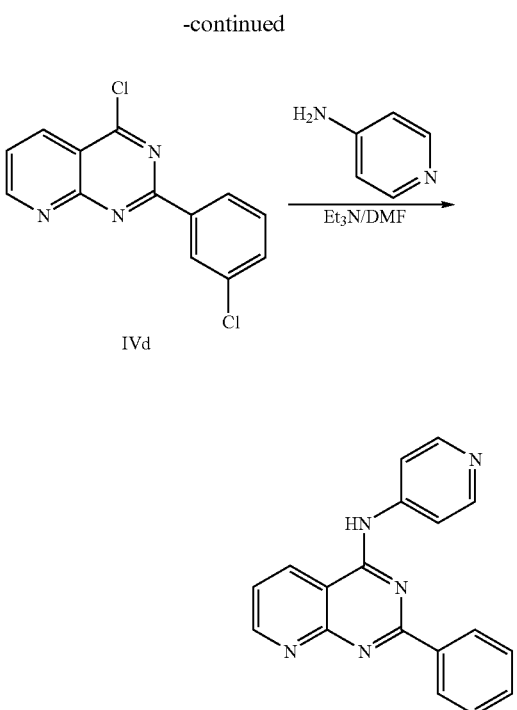
33
Reaction Scheme V
Alternate Procedure to Final
Product Employing Buchwald Coupling
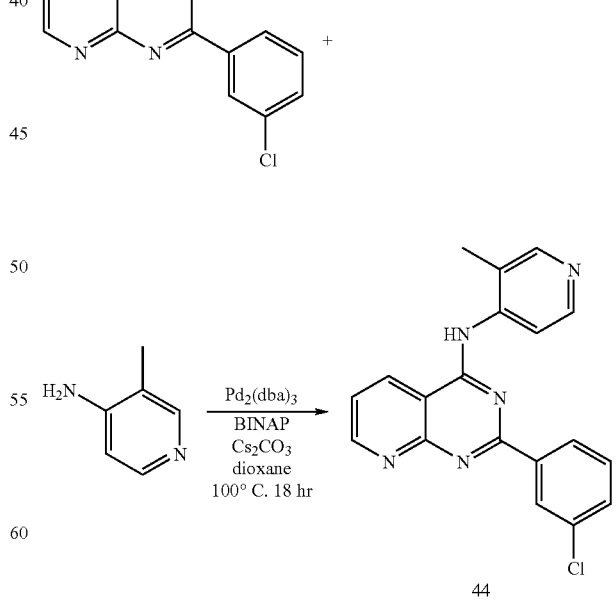
44
This general scheme was used for the synthesis of compounds using different acid chlorides.

Reaction Scheme V
Alternate Procedure to Final Product
Employing Displacement with Boc-4-amino-3-picoline

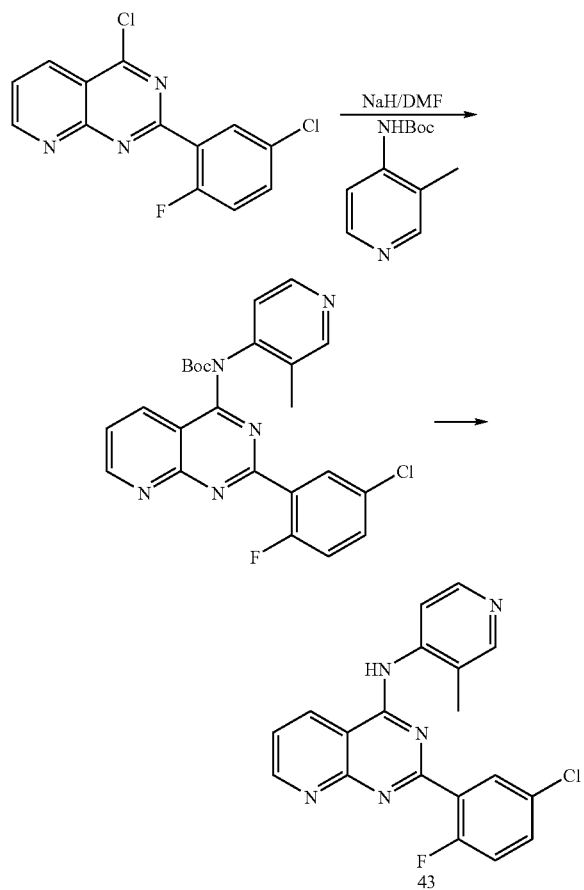

While the foregoing exemplary Reaction Schemes are set forth to illustrate the synthetic methods of the invention, it is understood that the substituents shown on the quinazoline derivative ring of the products are generically of the formula (1) as described herein and that the reactants may be substituted accordingly.

The following examples are intended to illustrate, but not to limit, the invention.

EXAMPLE 1

Examples 1–4 illustrates Reaction Scheme 1 where the substituents are as listed in the Table below. The compounds in bold are found in the Reaction Schemes.

| Compound | R Substitution | R2 Substitution |
|---|---|---|
| Ib, If, Ij, 17 | para F | H |
| Ic, Ig, Ik, 12 | meta CF3 | H |
| Id, Ih, Il, 11 | ortho Cl | H |
| Ie, Ii, Im, 13 | meta F | H |

Synthesis of Compound 17

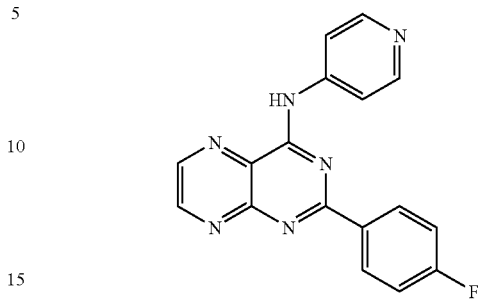

Pyridine (2.1 mL, 0.025 mol) was added to methyl 3-amino-2-pyrazine carboxylate Ia (3 g, 0.020 mol) in dry CHCl$_3$ (50 mL) and stirred for 5 minutes under nitrogen at room temperature. 4-fluorobenzoyl chloride (3.5 mL, 0.029 mol) was added slowly to the reaction mixture. The mixture was stirred for 18 hours under nitrogen. The reaction mixture was washed with 5% Na$_2$CO$_3$ solution (2×200 mL), water (2×200 mL), brine (2×200 mL), dried (MgSO$_4$) and the solvent was removed in vacuo. The desired product Ib was obtained by re-crystallization from ethyl acetate (1.6 g, 30% yield). EIMS: M+ 275

NH$_4$OH (28% NH$_3$ in H$_2$O, 10 mL) was added to a stirred suspension of the amide Ib (0.69 g) in EtOH (30 mL) and stirred for 1 hr. 10M NaOH (2 mL) was added and refluxed for 1 hr. The solvent was removed in vacuo. The solid was re-suspended in water and acidified with 4M HCl until the solution was at pH 1. The product If was filtered and washed with water and acetone and dried in vacuo at 45° C. for 18–24 hours (0.25g, 42% yield) EIMS: M+=242

Thionyl chloride (0.4 mL, 0.005 mol) was added to the stirred suspension of the pyrimidone If (0.25 g, 0.001 mol) in dry CHCl$_3$ (15 mL) and dry DMF (0.5 mL). The reaction mixture was refluxed under nitrogen for 1 hour. The solvent was removed in vacuo to give solid Ij which was dried on the high vacuum pump for 1 hour and directly used in the next reaction 4-aminopyridine (0.126 g, 0.001 mol) was added to the imino chloride Ij (0.269 g) in triethylamine (0.3 mL, 0.02 mol) and DMF (5 mL). The reaction mixture was then immediately heated to 160° C. for 15 minutes under nitrogen. CHCl$_3$ (100 mL) was added and the organic layer was washed with water (3×100 mL) and dried (MgSO$_4$). The solvent was removed in vacuo. The solid was purified by silica gel column chromatography, eluant 20: 1 CHCl$_3$: MeOH to give the product 17 (0.11 g, 36% over 2 steps). [M]$^+$=319

EXAMPLE 2

Synthesis of Compound 12

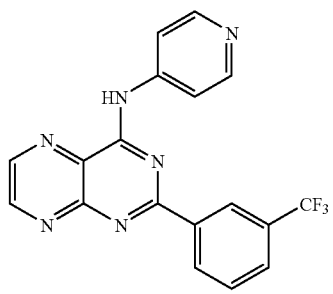

Pyridine (2.7 mL, 0.034 mol) was added to methyl 3-amino-2-pyrazine carboxylate Ia (4 g, 0.026 mol, 1 eq) in dry CHCl$_3$ (50 mL) and stirred for 5 minutes under nitrogen at room temperature. 3-(trifluoromethyl) benzoyl chloride (7.88 mL, 0.052 mol) was added slowly to the reaction mixture. The mixture was stirred for 18 hours under nitrogen. The reaction mixture was washed with 5% Na$_2$CO$_3$ solution (2×200 mL), water (2×200 mL), brine (2×200 mL), dried (MgSO$_4$) and the solvent was removed in vacuo. The desired product Ic was obtained by re-crystallization from ethyl acetate (1.94, 23% yield). EIMS: M+=325

NH$_4$OH (28% NH$_3$ in H$_2$O, 15 mL) was added to a stirred suspension of the amide Ic (1.94 g) in EtOH (30 mL) and stirred for 1 hr. 10M NaOH (3 mL) was added and refluxed for 1 hr. The solvent was removed in vacuo. The solid was re-suspended in water and acidified with 4M HCl until the solution was at pH 1. The product Ig was filtered and washed with water and acetone and dried in vacuo at 45° C. for 18–24 hours (0.64 g, 38% yield).

Thionyl chloride (0.7 mL, 0.01 mol) was added to the stirred suspension of the pyrimidone Ig (0.635 g, 0.002 mol) in dry CHCl$_3$ (20 mL) and dry DMF (0.2 mL). The reaction mixture was refluxed under nitrogen for 1 hour. The solvent was removed in vacuo to give solid Ik which was dried on the high vacuum pump for 1 hour and directly used in the next reaction. ESMS M+=310.89

4-aminopyridine (0.266 g, 0.002 mol) was added to the imino chloride Ik(0.675 g) in triethylamine (0.6 mL, 0.004 mol) and DMF (5 mL). The reaction mixture was then immediately heated to 160° C. for 15 minutes under nitrogen. CHCl$_3$ (50 mL) was added and the organic layer was washed with water (3×100 mL) and dried (MgSO$_4$). The solvent was removed in vacuo. An 80 mg aliquot crude sample was purified by preparative HPLC. 12 (30 mg). [M]+=368.93

EXAMPLE 3

Synthesis of Compound 10

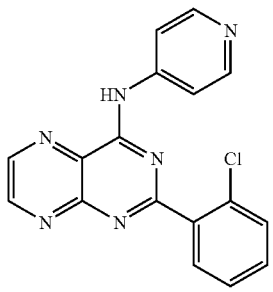

Pyridine (2.7 mL, 0.034 mol) was added to methyl 3-amino-2-pyrazine carboxylate Ia (4 g, 0.026 mol) in dry CHCl$_3$ (50 mL) and stirred for 5 minutes under nitrogen at room temperature. 2-Chlorobenzoyl chloride (6.6 mL, 0.052 mol) was added slowly to the reaction mixture. The mixture was stirred for 18 hours under nitrogen. The reaction mixture was washed with 5% Na$_2$CO$_3$ solution (2×200 mL), water (2×200 mL), brine (2×200 mL), dried (MgSO$_4$) and the solvent was removed in vacuo. The desired product Id was obtained silica gel chromatography 1:1 hexane: ethyl acetate (1.65 g, 21% yield). EIMS M-Cl=256.

NH$_4$OH (28% NH$_3$ in H$_2$O, 15 mL) was added to a stirred suspension of the amide Id (0.88 g) in EtOH (20 mL) and stirred for 1 hr. 10M NaOH (2 mL) was added and refluxed for 1 hr. The solvent was removed in vacuo. The solid was re-suspended in water and acidified with 4M HCl until the solution was at pH 1. The product Ih was filtered and washed with water and acetone and dried in vacuo at 45° C. for 18–24 hours (0.56 g, 71% yield). EIMS: M+=258

Thionyl chloride (0.13 mL, 0.002 mol) was added to the stirred suspension of the pyrimidone Ih (0.1 g, 0.0004 mol) in dry CHCl$_3$ (10 mL) and dry DMF (0.1 mL). The reaction mixture was refluxed under nitrogen for 0.5 hour. The solvent was removed in vacuo to give solid Il which was dried on the high vacuum pump for 1 hour and directly used in the next reaction. (100 mg) 4-aminopyridine (0.029 g, 0.0003 mol) was added to the imino chloride Il (0.053 g) in triethylamine (0.05 mL, 0.0004 mol) and DMF (10 mL). The reaction mixture was then immediately heated to 160° C. for 15 minutes under nitrogen. CHCl$_3$ (20 mL) was added and the organic layer was washed with water (3×50 mL) and dried (MgSO$_4$). The solvent was removed in vacuo. A sample of the crude solid was purified by preparative HPLC.(11, 4 mg) [M]+=334.95

EXAMPLE 4

Synthesis of Compound 13

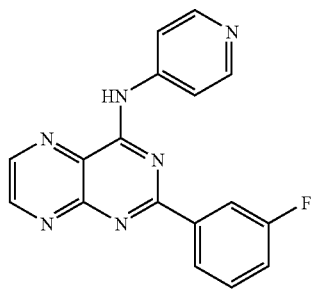

Pyridine (2.7 mL, 0.034 mol) was added to methyl 3-amino-2-pyrazine carboxylate Ia (4 g, 0.026 mol) in dry CHCl$_3$ (50 mL) and stirred for 5 minutes under nitrogen at room temperature. 3-fluorobenzoyl chloride (6.35 mL, 0.052 mol) was added slowly to the reaction mixture. The mixture was stirred for 18 hours under nitrogen. The reaction mixture was washed with 5% Na$_2$CO$_3$ solution (2×200 mL), water (2×200 mL), brine (2×200 mL), dried (MgSO$_4$) and the solvent was removed in vacuo. The desired product Ie was obtained by re-crystallization from ethyl acetate (1.68 g, 23% yield). EIMS: M+=275.

NH$_4$OH (28% NH$_3$ in H$_2$O, 15 mL) was added to a stirred suspension of the amide Ie (1.68 g) in EtOH (45 mL) and stirred for 1 hour. 10M NaOH (3 mL) was added and refluxed for 1 hour. The solvent was removed in vacuo. The solid was re-suspended in water and acidified with 4M HCl until the solution was at pH 1. The product Ii was filtered and washed with water and acetone and dried in vacuo at 45° C. for 18–24 hours (0.92 g, 61%).

Thionyl chloride (0.7 mL, 0.01 mol) was added to the stirred suspension of the pyrimidone Ii (0.5 g, 0.002 mol) in dry CHCl$_3$ (20 mL) and dry DMF (0.2 mL). The reaction mixture was refluxed under nitrogen for 1.0 hour. The solvent was removed in vacuo to give solid Im which was dried on the high vacuum pump for 1 hour and directly used in the next reaction. (540mg) 4-aminopyridine (0.252 g, 0.0027 mol) was added to the imino chloride Im(0.540 g) in triethylamine (0.6 mL, 0.004 mol) and DMF (5 mL). The reaction mixture was then immediately heated to 160° C. for 15 minutes under nitrogen. CHCl₃ (20 mL) was added and the organic layer was washed with water (3×50 mL) and dried (MgSO₄). The solvent was removed in vacuo. An 80 mg aliquot crude sample was purified by preparative HPLC (13, 12 mg) [M]+=318.91.

Different acid chlorides were used to generate different amides (e.g. Ib). Differentially substituted 4-aminopyridines were used to generate differently substituted analogs. (e.g. 7, 8, 20, 21, and 22).

EXAMPLE 5

Synthesis of Compounds 23 and 25

This example illustrates Reaction Scheme II.

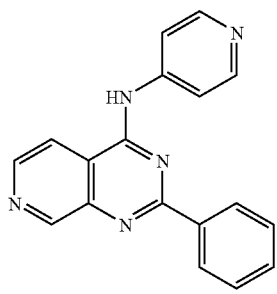

23

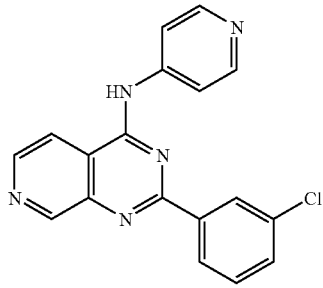

25

Preparation of IIa:

Ethyl 1-benzyl-3-oxo-4-piperidine carboxylate-HCl (10 g, 33.58 mmole, 1 eq) was added to a solution of 25% sodium methoxide in methanol (4 eq) while cooling reaction mixture on an ice bath. Benzamidine hydrochloride was added slowly followed by dilution of reaction mixture to 200 ml with ethanol. The reaction mixture was refluxed overnight, followed by evaporation to dryness, residue was taken up in water extracted with dichloromethane (2×50 ml). Combined extracts were dried over sodium sulfate (anh) and solvent removed to give 1.4 g tan solid. Ethyl acetate was added to the aqueous layer which caused the precipitation of a white solid. Solid was isolated and washed with a small amount of methanol and vacuum dried to give 8.5 g product (80%). Compound 25 was prepared in an analogous fashion using 3-Chlorobenzamidine hydrochloride in place of benzamidine hydrochloride.

Preparation of IIb:

Removal of benzyl group from IIa was accomplished as follows. IIa (3.0 g, 9.5 mmole) was dissolved in acetic acid. 300 mg of 10% Pd/C catalyst was added and hydrogenation was carried out at 45° C. for 4 hours. Removed catalyst by filtration over celite. Evaporated acetic acid to give product as white solid 3.4 g (acetate salt) (80% yield).

Preparation of IIc:

IIb (3.4 g 15 mmole) was suspended in m-xylene, added 10% Pd/C (3.0 g) and refluxed for 6 hours. Removed catalyst by filtration over celite. Removed solvent to give 1.3 g product (38%).

Preparation of IId:

IIc (446 mg, 2 mmole) was suspended in phosphorous oxychloride (8 ml) and heated to reflux for 15 minutes. Removed excess phosphorous oxychloride under vacuum. Residue was treated with ice water, extracted with chloroform. Combined chloroform extracts were washed with water, dried over sodium sulfate (anh.) and solvent removed under vacuum to give 494 mg product.

Preparation of 23:

IId (494 mg, 2.05 mmole) was suspended in isopropanol (5 ml), added 4-aminopyridine (192 mg, 2.05 mmole), 6 ml dimethyl formamide, 0.25 ml triethylamine and heated to 50° C. for 20 minutes. Cooled reaction mixture was filtered, product washed with 1 ml methanol, dried to give 373 mg. This material was purified by reversed phase HPLC to give 129 mg product.

EXAMPLE 6

Synthesis of Compound 24

This example illustrates Reaction Scheme III.

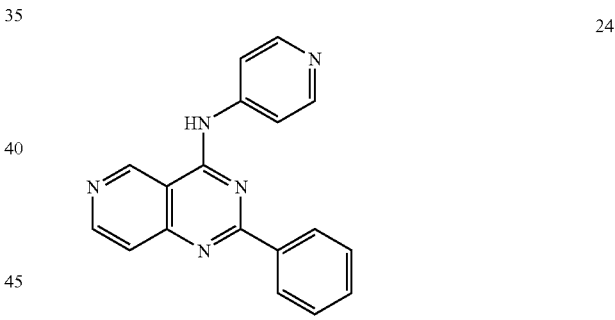

24

Preparation of IIIa:

Methyl 1-benzyl-oxo-3-piperidine carboxylate HCl (11.27 g, 39.72 mmole) was added to a solution of 25% sodium methoxide (31 ml, 4 eq) in methanol while cooling the reaction mixture in an ice bath. Added benzamidine HCl (6.93 g, 39.72 mmole) slowly then diluted the mixture to 200 ml with ethanol. Refluxed the reaction 4 hours. Removed ethanol under vacuum, residue was taken up in dichloromethane and water, extracted with dichloromethane, combined dichloromethane extracts dried over sodium sulfate (anh) and evaporated to dryness to give 4.36 g product. Ethyl acetate was added to aqueous layer to give a white solid which was washed with minimum amount of chloroform to give 3.65 g product. A second crop was obtained upon standing overnight 3.92 g. Total yield 7.57 g (61% yield).

Preparation of IIIb:

IIIa (3.5 g, 11.03 mmole) was dissolved in 80 ml acetic acid, added 400 mg 10% Pd/C and hydrogenated at 40 psi at 50° C. for 5 hours. Filtered mixture over celite to remove catalyst. Evaporated acetic acid to give product as acetate salt. 3.7 g (97% yield).

Preparation of IIIc:

IIIb (3.5 g) was dissolved in water, added ethyl acetate, basified with 1M NaOH to pH 9. Free base of IIIb was extracted with ethyl acetate, then dichloromethane, combined extracts dried over sodium sulfate (anh.). Removed solvent to give the free base of IIIb. This was suspended in m-xylene (60 ml) added 10% Pd/C (500 mg) and refluxed for 1.5 days. Removed catalyst by filtration over celite. Removed xylene under vacuum to give product (700 mg).

Preparation of IIId:

The pyridopyrimidone IIIc (500 mg) was suspended in phosphorous oxychloride (5 ml) and heated to reflux for 4 hours at which time all starting material was dissolved in solution. Removed excess phosphorous oxychloride under vacuum. The residue was treated with ice (50 ml) chloroform (50 ml), mixture neutralized with addition of 10% sodium bicarbonate. Washed chloroform with 10% sodium bicarbonate, dried chloroform over sodium sulfate (anh). Removed solvent to give crude product. This material was chromatographed on silica gel eluting with chloroform to give 62 mg product.

Synthesis of 24:

Iminochloride IIId (60 mg, 0.248 mmole) was combined with 4-aminopyridine (46.7 mg, 0.496 mmole, 2 eq) in 2 ml dimethylformamide. Added 86 microliters diisopropylethylamine and heated to 60° C. for 1 hour. Reaction mixture was subjected to HPLC purification on reversed phase HPLC to give the purified product.

EXAMPLE 7

Synthesis of Compound 33

General Method for the Synthesis of Compounds 26–44

This example illustrates Reaction Scheme IV.

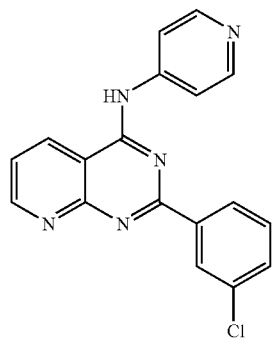

33

Preparation of IVa:

2-Amino nicotinic acid (50 g, 0.362 mole) was dissolved in 500 ml methanol and treated with thionyl chloride (66 ml, 107.6 g, 0.905mole) dropwise over 30 min. Reaction mixture was heated to reflux for 3 days. Removed solvent under vacuum, residue taken up in chloroform, washed with 5% HCl (50 ml), 10% sodium bicarbonate (50 ml), water, and chloroform layer dried over sodium sulfate (anh). Removed solvent to give 27 g product (49.1% yield).

Preparation of IVb:

2-aminonicotinic acid methyl ester (6.4 g, 42 mmole) was dissolved in chloroform (50 ml) treated with triethylamine (6.25 ml, 45 mmole) followed by dropwise addition of 3-Chlorobenzoyl chloride (7.8 g, 45 mmole) dissolved in 10 ml chloroform. The reaction mixture was stirred for 2 days at room temperature, washed reaction mixture with 10% sodium bicarbonate, 5% HCl, water. Dried chloroform layer over sodium sulfate (anh), removed solvent to give an oil. Trituration with 30% ethyl acetate in hexanes gave the product as a solid, which was isolated by filtration to give 12.4 g product Preparation of IVc:

The amide IVb (6.81 g, 23.4 mmole) was suspended in methanol (10 ml) treated with 25 ml 28% ammonium hydroxide. Heated reaction mixture for 4 hours then added 25 ml 28% ammonium hydroxide Sodium hydroxide and refluxed overnight. Upon cooling a white solid was deposited. Removed methanol, filtered solid to give product 2.8 g Preparation of IVd:

Similar to the preparation of IIId.

Preparation of 33:

Similar to the preparation of compound 24.

Twenty-eight different acid chlorides were used to generate different amides (e.g. IVb). Differentially substituted 4-aminopyridines were used to generate differently substituted analogs (e.g. compounds 43 and 44).

EXAMPLE 8

Synthesis of Compounds 43 and 44

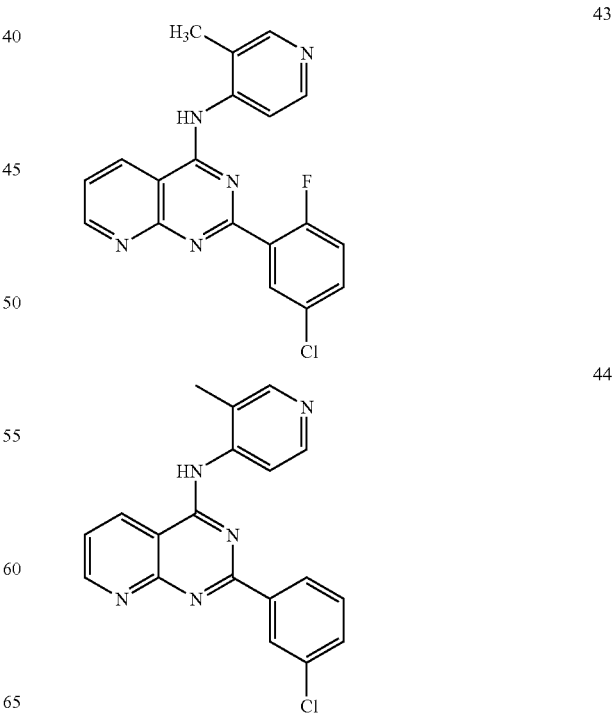

This example illustrates Reaction Scheme V.

Preparation of 43:
4-Chloro-2-(2-fluoro-5-Chlorophenyl)pyridopyrimidine was used as the partner in the Buchwald coupling step, shown above, to prepare compound 43.

Preparation of 44:
IVd, 4-Chloro-2-(3-Chlorophenyl)pyridopyrimidine (294 mg, 1 mmole) was suspended in 8 ml dioxane, followed by addition of 4-aminopicoline (129 mg, 1.2 mmole), 2,2'Bis (diphenylphosphino)-1,1'-binaphthalene (BINAP, 4.66 mg, 0.0075 mmole). Tris(dibenzylidene acetone)dipalladium(0) (Pd$_2$(dba)$_3$ 2.2 mg, 0.0025 mmole) and cesium carbonate (456 mg, 1.4 mmole). The mixture was stirred at 100° C. under an inert atmosphere for 18 hr. Reaction mixture was filtered over celite and product was isolated by preparative reversed phase HPLC.

EXAMPLE 9

Alternate Synthesis of Compound 43

Preparation of Boc-4-amino-3-picoline:

3-Methyl-4-aminopyridine (20.00 g, 0.185 mol) in dry THF (150 mL) was added a solution of Di-tert-butyl dicarbonate (Acros, 97% purity) (45.80 g, 0.203 mol) in dry THF (50 mL). The resultant pale yellow solution was left stirred at room temperature for 3 hours before being evaporated. The solid that resulted was suspended in hexane (200 mL) and filtered. The solid was washed further with hexane (4×200 mL) to remove last traces of excess reagent, and dried under high vacuum. The product was a yellow crystalline solid (29.93 g, 78% yield).

Preparation of [2-(5-Chloro-2-fluoro-phenyl)-pyrido [2,3-d]pyrimidin-4-yl]-(3-methyl-pyridin-4-yl)-carbamic acid tert-butyl ester Sodium hydride (3.78 g, 94.5 mmol) was placed in a three neck round bottom flask. The system was purged with nitrogen and cooled to 0° C. 180 mL of dry DMF was introduced to the reaction mixture, followed by the addition of a solution of Boc-picoline (13.11 g, 62.95 mmol) in DMF (125 mL). This mixture was stirred for 20 minutes at the temperature of an ice bath. At this time the imino chloride (19.4 g, 65.95 mmol) was added, as a solid in four equal portions. The additions were separated by 2 minutes. After the addition of the imino chloride is complete the ice bath was removed. The reaction mixture was stirred for an additional 4 hours at room temperature. The reaction mixture was then quenched with 600 mL water. To the quenched reaction mixture was added 800 mL ethyl acetate. The ethyl acetate layer (which contains the product) was washed 4×200 mL, with brine and dried over anhydrous magnesium sulfate, filtered and concentrated to an oily solid. This material was purified using silica gel chromatography. Crude material was dissolved in Ethyl acetate.

Elution with ethyl acetate/hexane (1:1), when the desired spot started to elute the solvent ratio was changed to ethyl acetate/hexane (8:2), then followed by pure ethyl acetate. Fractions corresponding to the product were pooled and concentrated to give a white foam. 26 g. 72% yield.

Preparation of 43:
To a solution of HCl in ethylacetate (35 g of HCl in 1200 ml EtOAc) was added a solution of [2-(5-Chloro-2-fluoro-phenyl)-pyrido[2,3-d]pyrimidin-4-yl]-(3-methyl-pyridin-4-yl)-carbamic acid tert-butyl ester (90 g) in EtOAc (200 ml) and the mixture was stirred at room temperature for 3 days. The precipitate was filtered and washed with EtOAc (4×200 ml) to give a pale yellow solid (75 g, 97%) which was not further purified.

EXAMPLE 10

Synthesis of Compound 45

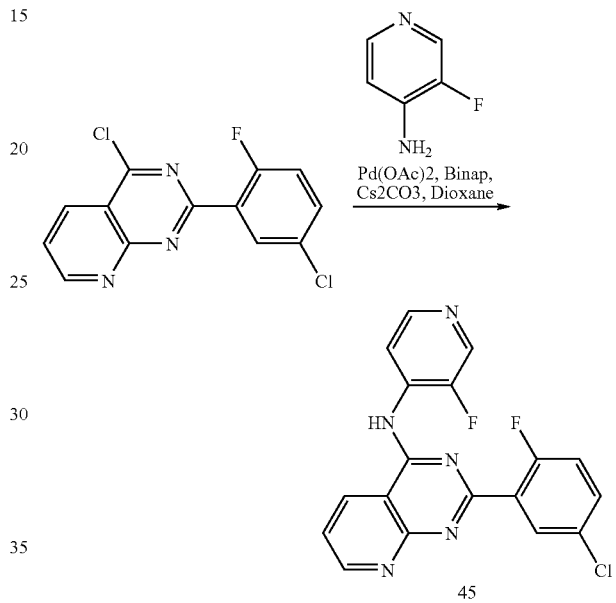

Preparation of [2-(5-Chloro-2-fluoro-phenyl)-pyrido [2,3-d]pyrimidin-4-yl]-(3-fluoro-pyridin-4-yl)-amine To a suspension of dioxane (5 ml), Pd(OAc)2 (50 mg), BINAP (20 mg), 4-amino-3-fluoro-pyridine (42 mg) and Cs2CO3 (200 mg) was added the crude imino chloride, 4-Chloro-2-(5-Chloro-2-fluoro-phenyl)-pyrido[2,3-d]pyrimidine (100 mg, 0.34 mmol) in a sealed tube. The reaction mixture was heated to 110° C. for 15 h. The reaction mixture was cooled to r.t. and filtered through Celite® and the crude material was purified by silica gel flash column chromatography (95% to 5% gradient CH2Cl2/EtOAc) to afford [2-(5-Chloro-2 -fluoro-phenyl)-pyrido[2,3-d]pyrimidin-4-yl]-(3-fluoro-pyridin-4-yl)-amine (27.3 mg).

Preparation of [2-(5-Chloro-2-fluoro-phenyl)-pyrido [2,3-d]pyrimidin-4-yl]-(3-bromo-pyridin-4-yl)-amine As above employing, 4-amino-3-bromo-pyridine as the 3-substituted 4-aminopyridine.

Preparation of 45:
As above employing, 4-amino-3-iodo-pyridine as the 3-substituted 4-aminopyridine.

EXAMPLE 11

Synthesis of Compound 46

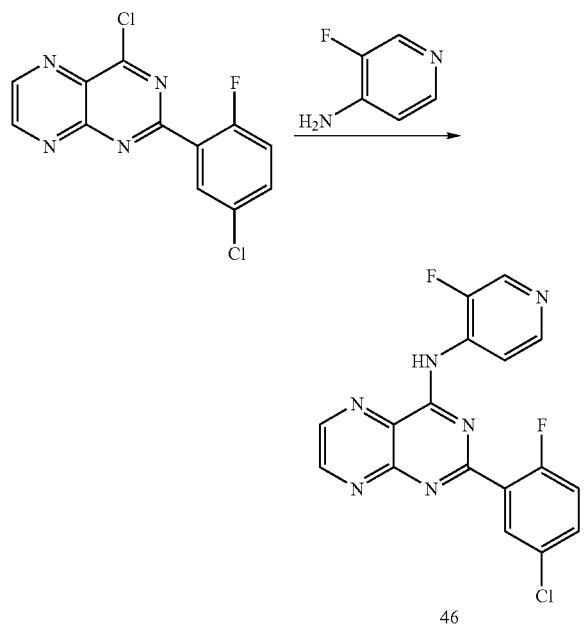

46

Preparation of 46:

To a suspension of dioxane (15 ml), Pd(OAc)$_2$ (100 mg), BINAP (100 mg), 4-amino-3-fluoro-pyridine (220 mg) and Cs$_2$CO$_3$ (1.0 g) was added the crude imino chloride, xxx (500 mg) in a sealed tube. The reaction mixture was heated to 100° C. for 20 h. The reaction mixture was cooled to r.t. and filtered through Celite® and the crude material was purified by silica gel flash column chromatography (95% to 5% gradient CH$_2$Cl$_2$/EtOAc) to afford [2-(5-Chloro-2-fluoro-phenyl)-pteridin-4-yl]-(3-fluoro-pyridin-4-yl)-amine (200 mg).

EXAMPLE 12

Synthesis of Compound 47

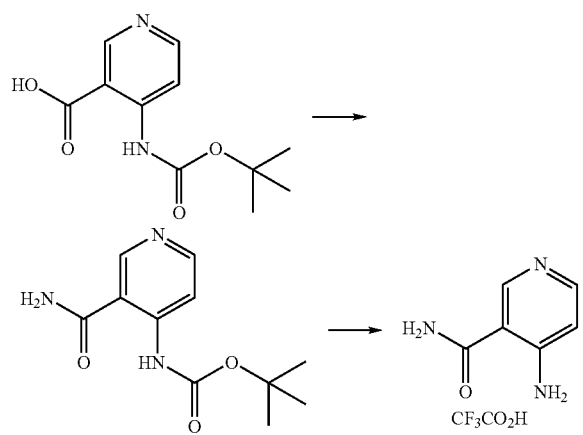

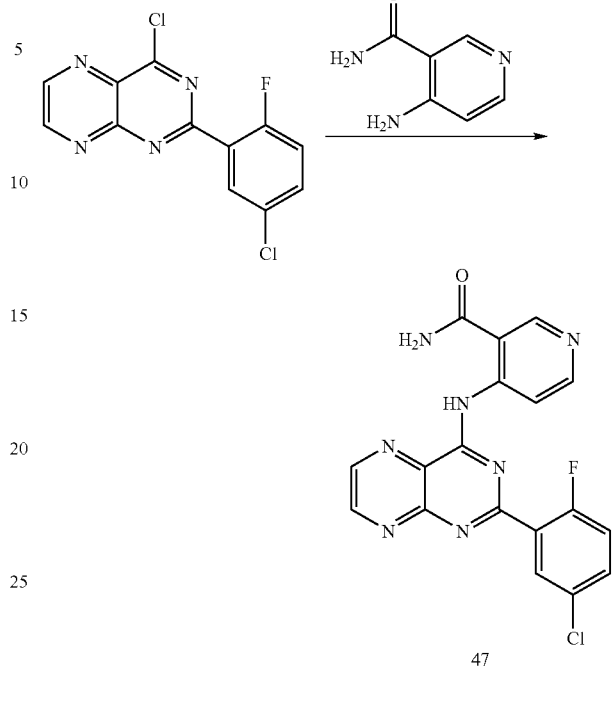

47

Preparation of 4-tert-Butoxycarbonylamino-nicotinic acid

To a solution of 4-tert-Butoxycarbonylamino-nicotinic acid methyl ester (6.02 g, 23.86 mmol) in dioxane (100 mL) was added aq. sodium hydroxide (0.970N solution, 28.05 mL, 27.20 mmol). The solution was heated to 60° C. for 1 hr then cooled. Aqueous hydrochloric acid (1.031M solution, 26.99 mL, 27.20 mmol) was added and the mixture was extracted with chloroform (5×100 mL). The extracts were dried (MgSO$_4$) and evaporated to give 4-tert-Butoxycarbonylamino-nicotinic acid, a cream solid (4.70 g, 83% yield) without further purification.

Preparation of 4-Amino nicotinamide 4-tert-Butoxycarbonylamino-nicotinic acid (1.0 g, 4.20 mmol) was suspended in dry DMF (50 mL) followed by carbonyl-diimidazole (CDI, 1.36 g, 8.40 mmol). The mixture was heated to 60° C. for 1 h, then cooled. Dry ammonia gas was slowly bubbled through this solution for 1 h, followed by evaporation of the mixture. The residue was dissolved in water (20 mL)/chloroform (50 mL) and shaken then the layers separated. The aqueous layer was extracted further with chloroform (3×50 mL) and the combined organic extracts dried (MgSO$_4$) and evaporated to give a yellow oily solid. Silica gel chromatography (CH$_2$Cl$_2$, 0–15% MeOH gradient) gave the desired product, (3-Carbamoyl-pyridin-4-yl)-carbamic acid tert-butyl ester, as a yellow solid. This material was directly treated with trifluoroacetic acid (TFA, 20 mL) stirred at r.t. for 45 min., then evaporated to give the desired amine, 4-Amino nicotinamide, as its TFA salt (892 mg, 85% yield over 2 steps).

Preparation of 47:

The 4-Chloro-2-(5-Chloro-2-fluoro-phenyl)-pteridine (200 mg), Pd2(dba)$_3$ (31 mg) and BINAP (33 mg) were suspended in dioxane (20 mL) under N$_2$. The 4-aminonicotinamide (256 mg) in dioxane (90 mL) was added followed by Cs$_2$CO$_3$ (665 mg). The mixture was then heated to 100° C. under N$_2$ for 18 hours. The warm reaction mixture was then filtered through Celite and the Celite pad was washed with methanol. The filtrate was then concentrated in vacuo to and the residue was purified by reverse phase HPLC (CH$_3$CN: H$_2$O). The fractions containing pure product were evaporated to dryness, dissolved in CHCl$_3$/MeOH Product, and acidified with HCl/Et$_2$O. The mixture was evaporated to dryness to afford the HCl salt of 4-[2-(5-Chloro-2-fluoro-phenyl)-pteridin-4-ylamino]-nicotinamide (10 mg).

EXAMPLE 13

Assay for TGF-β Inhibition

The ability of invention compounds to inhibit TGF can be evaluated in a TGF β1 kinase autophosphorylation protocol. This assay can be conducted as follows: Compound dilutions and reagents are prepared fresh daily. Compounds are diluted from DMSO stock solutions to 2 times the desired assay concentration, keeping final DMSO concentration in the assay less than or equal to 1%. TGF β1 kinase is diluted to 4 times the desired assay concentration in buffer+DTT. ATP is diluted into 4x reaction buffer, and gamma-33P-ATP is added at 60 uCi/mL.

The assay is performed by adding 10 ul of the enzyme to 20 ul of the compound solution. The reaction is initiated by the addition of 10 ul of ATP mix. Final assay conditions include 10 uM ATP, 170 nM TGF β1 kinase, and 1 M DTT in 20 mM MOPS, pH7. The reactions are then incubated at room temperature for 20 minutes afterwhich they are stopped by transferring 23 ul of reaction mixture onto a phosphocellulose 96-well filter plate, (pre-wetted with 15 ul of 0.25M H3PO4 per well). After 5 minutes, the wells are washed 4x with 75 mM H3PO4 and once with 95% ethanol. The plate is dried, scintillation cocktail is added to each well, and the wells are counted in a Packard TopCount microplate scintillation counter. The ability of a compound to inhibit the enzyme is determined by comparing the counts obtained in the presence of compound to those of the positive control (in the absence of compound) and the negative control (in the absence of enzyme).

EXAMPLE 14

Assay for TGF-β Inhibition

Invention compounds can also be evaluated by measuring their abilities to inhibit the phosphorylation of the substrate casein. The assay can be conducted as follows: Compound dilutions and reagents are prepared fresh daily. Compounds are diluted from DMSO stock solutions to 2 times the desired assay concentration, keeping final DMSO concentration in the assay less than or equal to 1%. TGF β1 kinase is diluted to 4 times the desired assay concentration in buffer+DTT. ATP and casein are diluted into 4x reaction buffer, and gamma-33P-ATP is added at 50 uCi/mL.

The assay is performed by adding 10 ul of the enzyme to 20 ul of the compound solution. The reaction is initiated by the addition of 10 ul of the casein/ATP mix. Final assay conditions included 2.5 uM ATP, 100 uM casein, 6.4 nM TGF β1 kinase, and 1M DTT in 20 mM Tris buffer, pH 7.5. The reactions are incubated at room temperature for 45 minutes. The reactions are then stopped by transferring 23 ul of reaction mixture onto a phosphocellulose 96-well filter plate, which had been pre-wetted with 15 ul of 0.25M H3PO4 per well. After 5 minutes, the wells are washed 4x with 75 mM H3PO4 and once with 95% ethanol. The plate is dried, scintillation cocktail is added to each well, and the wells are counted in a Packard TopCount microplate scintillation counter. The ability of a compound to inhibit the enzyme is determined by comparing the counts obtained in the presence of the compound to those of the positive control (in the absence of compound) and the negative control (in the absence of enzyme).

In both of the assays referenced above, IC$_{50}$ values can be determined with curve-fitting plots available with common software packages. Approximate IC$_{50}$ values can be calculated using formula $$IC_{50}(app) = A \times i/(1-A)$$

where A=fractional activity and i=total inhibitor concentration.

The compounds in Table 5 have been found to exhibit IC$_{50}$ values of less than 5 μM relative to TGFβ.

What is claimed is:
1. A compound of the formula:

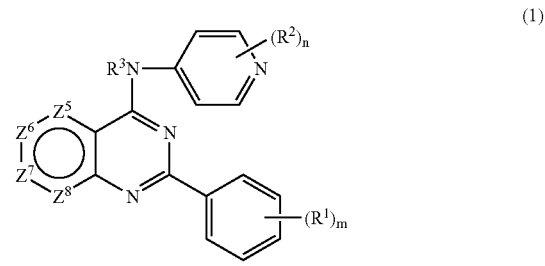

or the pharmaceutically acceptable salts thereof;
wherein each of $Z^5$, $Z^6$, $Z^7$ and $Z^8$ is N or CH and wherein two $Z^5$, $Z^6$, $Z^7$ and $Z^8$ are N and wherein two adjacent Z positions cannot be N;
wherein m and n are each independently 0–3;
wherein each $R^1$ is independently OH, SH, NH$_2$, OR, SR, NHR, halo or R-halide;
wherein two adjacent $R^1$ groups may be joined to form an aliphatic hetero cycle ring of 5–6 members;
wherein each $R^2$ is independently R, halo, R-halide, OR-halide, NH$_2$, CONH$_2$ or CONHR;
wherein R is optionally substituted C$_1$–C$_{12}$ alkyl, C$_1$–C$_{12}$ alkenyl, C$_1$–C$_{12}$ alkynyl, or aryl C$_1$–C$_{12}$ alkyl, containing 0–4 heteroatoms in place of a carbon in the carbon backbone, where the optional substituents are =O, =N, or OH; and
wherein $R^3$ is H or CH$_3$;
with the provio that
when $Z^5$ and $Z^8$ are N and $Z^6$ and $Z^7$ are CH, when $R^3$ is H, and when the pyridyl is unsubstituted, then the phenyl is substituted.
2. The compound of claim 1 wherein
$R^1$ is selected from the group consisting of H, fluoro, chloro, bromo, iodo, methoxy, ethoxy, isopropoxy, and the trifluoro methyl or
wherein two $R^1$ form a fused 1,3, dioxolane ring.
3. The compound of claim 1 wherein $R^1$ is one or more halos.
4. The compound of claim 1 wherein $R^1$ is independently one or more alkyls, alkyl halides, alkoxys or O-alkyl phenyls.
5. The compound of claim 1 wherein m is 0, n is 1, and $R^2$ is positioned at the 3' position of the pyridyl.

6. The compound of claim 1 wherein m is 1 or 2 and $R^1$ is positioned at the 2' or 5' position of the phenyl moiety.

7. The compound of claim 1 wherein each $R^2$ is independently a hydrocarbyl residue (1–6C) containing 0–2 heteroatoms selected from O, S and N.

8. The compound of claim 7 wherein each $R^2$ is independently alkyl, $CONH_2$, CONHR, or halo.

9. The compound of claim 1 where $R^2$ is selected from the group consisting of methyl, ethyl, $CONH_2$ and bromo.

10. The compound of claim 1 wherein m and n are each independently 0–2.

11. The compound of claim 1 where n is 0.

12. The compound defined in claim 1 having the formula:

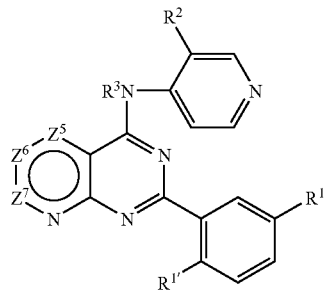

or the pharmaceutically acceptable salts thereof;

wherein each of $Z^5$, $Z^6$ and $Z^7$ is N or CH and wherein one of $Z^5$, $Z^6$ and $Z^7$ is N and wherein two adjacent Z positions cannot be N;

wherein $R^1$ is F, Cl, Br, I or $CH_3$;

wherein $R^{1'}$ is Br, F or Cl; and wherein $R^2$ is not present, is $CH_3$ or is an electron-withdrawing group.

13. The compound defined in claim 12 wherein $R^2$ is not present or is $CH_3$, F, Cl, $OCF_2H$, $OCF_3$, $CF_3$, CONHR or $CONH_2$; wherein R is optionally substituted $C_1$–$C_{12}$ alkyl, $C_1$–$C_{12}$ alkenyl, $C_1$–$C_{12}$ alkynyl, or aryl $C_1$–$C_{12}$ alkyl, containing 0–4 heteroatoms in place of a carbon in the carbon backbone, where the optional substituents are =O, =N, or OH.

14. The compound defined in claim 13 wherein $R^1$ is Cl and $R^{1'}$ is F.

15. A pharmaceutical composition, comprising a therapeutically effective amount of a compound of claim 1, and at least one pharmaceutically acceptable carrier.

* * * * *